United States Patent
Van Eperen et al.

(10) Patent No.: US 6,235,137 B1
(45) Date of Patent: May 22, 2001

(54) PROCESS FOR MANUFACTURING AN ELASTIC ARTICLE

(75) Inventors: David James Van Eperen; Mark John Beitz, both of Appleton; Joseph Conrad Burriss, Neenah; Robert Thomas Cimini, Appleton; Chris Lee Heikkinen, Menasha; Daniel Hoo, Appleton; David Andrae Justmann, Hortonville; Richard Francis Keller, Fremont; Douglas Paul Rammer, Appleton; Lorry Francis Sallee, Pine River; Jeffrey Joseph Samida, Appleton; Donald LeRoy Smith, Hortonville; Raymond Gerard St. Louis, Fremont; Barbara Jean Wink, Winneconne, all of WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/327,369

(22) Filed: Jun. 4, 1999

Related U.S. Application Data

(60) Provisional application No. 60/131,773, filed on Apr. 30, 1999, and provisional application No. 60/095,499, filed on Aug. 6, 1998.

(51) Int. Cl.$^7$ ................................ A61F 13/49; B32B 7/14
(52) U.S. Cl. ...................... 156/176; 156/73.1; 156/73.2; 156/73.3; 156/160; 156/169; 156/178; 156/179; 604/365; 428/107
(58) Field of Search ................................ 156/73.1–73.3, 156/160–165, 166, 169, 171, 176, 177, 178, 179, 193, 250, 267, 269, 270, 271, 427, 436; 604/358, 365, 385.24, 385.26, 385.27; 428/107–109, 123

(56) References Cited

U.S. PATENT DOCUMENTS 3,901,236  8/1975  Assarsson et al. .
4,076,663  2/1978  Masuda et al. .

(List continued on next page.)

FOREIGN PATENT DOCUMENTS 0 217 032 A2  4/1987  (EP) .
0 532 002 B1  3/1993  (EP) .

(List continued on next page.)

OTHER PUBLICATIONS

Federal Test Method Standard (FTMS) No. 191A, Method 5514, "Water Resistance of Cloth; Low Range, Hydrostatic Pressure Method, " Jul. 20, 1078, 3 pages.

(List continued on next page.)

Primary Examiner—Michael W. Ball
Assistant Examiner—Jessica Rossi
(74) Attorney, Agent, or Firm—Paul Yee

(57) ABSTRACT

A distinctive method and apparatus for forming an article includes a moving of at least one first strand of material, such as strand (22), along an appointed machine-direction (34). The at least one first strand of material is attached to a base layer of material (42) to provide a substrate composite (40), and a laminate layer (44) can be placed adjacent the at least one first strand of material to provide a laminate composite web (48). In a particular aspect, at least one second strand of material, such as strand (56), can be moved along its appointed machine-direction, and the at least one second strand of material can be attached to the base layer (42). In another aspect, an appointed portion of the base layer (42) can be folded to substantially enclose the at least one second strand (56) with the base layer material. Alternatively or additionally, an appointed portion of the base layer (42) can be folded to substantially enclose the at least one first strand (22) and the laminate layer (44) with the base layer material. In a further aspect, at least one of the strands of material can be divided of into a plurality of strand segments to provide a substantially nongathering section of at least one of the strands.

20 Claims, 16 Drawing Sheets

U.S. PATENT DOCUMENTS

| | | |
|---|---|---|
| 4,286,082 | 8/1981 | Tsubakimoto et al. . |
| 4,585,448 | 4/1986 | Enloe . |
| 4,610,678 | 9/1986 | Weisman et al. . |
| 4,663,220 | 5/1987 | Wisneski et al. . |
| 4,699,823 | 10/1987 | Kellenberger et al. . |
| 4,704,116 | 11/1987 | Enloe . |
| 4,842,666 | 6/1989 | Werenicz . |
| 5,028,224 | 7/1991 | Pieper et al. . |
| 5,147,343 | 9/1992 | Kellenberger . |
| 5,226,992 | 7/1993 | Morman . |
| 5,340,648 | 8/1994 | Rollins et al. . |
| 5,399,219 | 3/1995 | Roessler et al. . |
| 5,486,166 | 1/1996 | Bishop et al. . |
| 5,490,846 | 2/1996 | Ellis et al. . |
| 5,501,756 | 3/1996 | Rollins et al. . |
| 5,507,909 | 4/1996 | Rollins et al. . |
| 5,525,175 * | 6/1996 | Blenke et al. ............... 156/161 |
| 5,540,796 | 7/1996 | Fries . |
| 5,549,592 | 8/1996 | Fries et al. . |
| 5,562,650 | 10/1996 | Everett et al. . |
| 5,595,618 | 1/1997 | Fries et al. . |
| 5,605,735 | 2/1997 | Zehner et al. . |
| 5,711,847 * | 1/1998 | Rajala et al. ............... 156/580.2 |
| 5,820,973 | 10/1998 | Dodge, II et al. . |
| 5,827,259 | 10/1998 | Laux et al. . |
| 5,882,573 | 3/1999 | Kwok et al. . |
| 5,902,540 | 5/1999 | Kwok . |
| 5,904,298 | 5/1999 | Kwok et al. . |
| 5,904,675 | 5/1999 | Laux et al. . |
| 5,993,433 | 11/1999 | St. Louis et al. . |
| 6,077,375 * | 6/2000 | Kwok ............... 156/161 |
| B2 3,860,003 | 6/1990 | Buell . |

FOREIGN PATENT DOCUMENTS

| | | |
|---|---|---|
| WO 94/18927 A1 | 9/1994 | (WO) . |
| WO 95/16425 A2 | 6/1995 | (WO) . |
| WO 96/05792 A1 | 2/1996 | (WO) . |
| WO 96/32084 A1 | 10/1996 | (WO) . |
| WO 97/18346 A1 | 5/1997 | (WO) . |
| WO 97/20532 A1 | 6/1997 | (WO) . |
| WO 99/20215 A1 | 4/1999 | (WO) . |

OTHER PUBLICATIONS

TAPPI Official Test Method T 543 om–94, "Bending Resistance of Paper (Gurley Type Tester), " published by the TAPPI Press, Atlanta, Georgia, pp. 1–7.

* cited by examiner

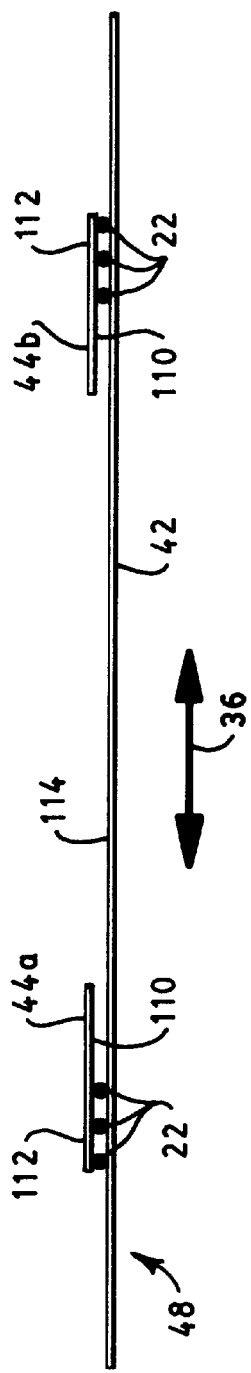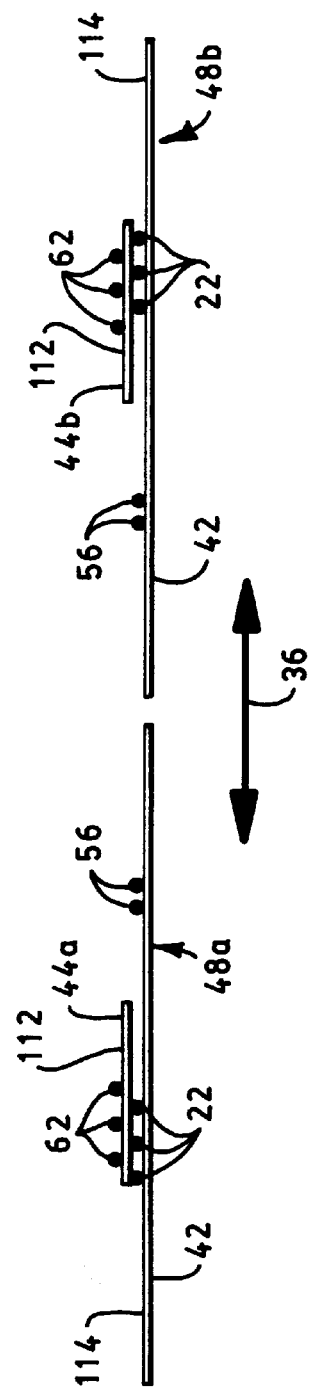

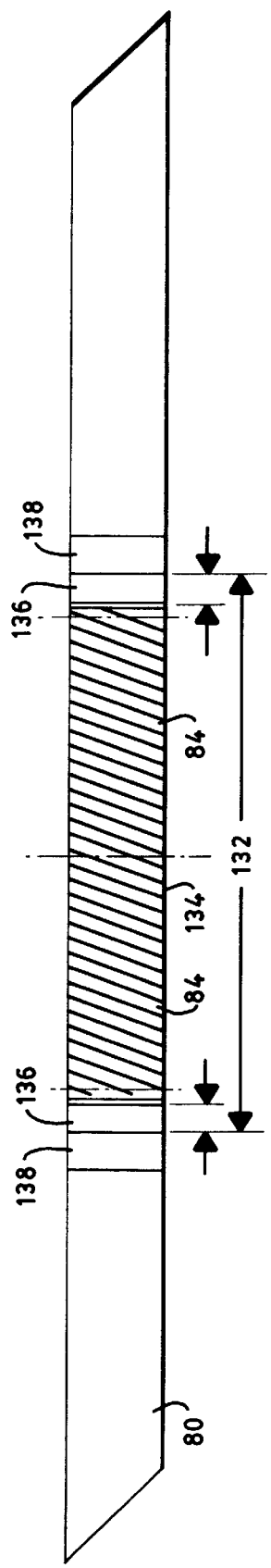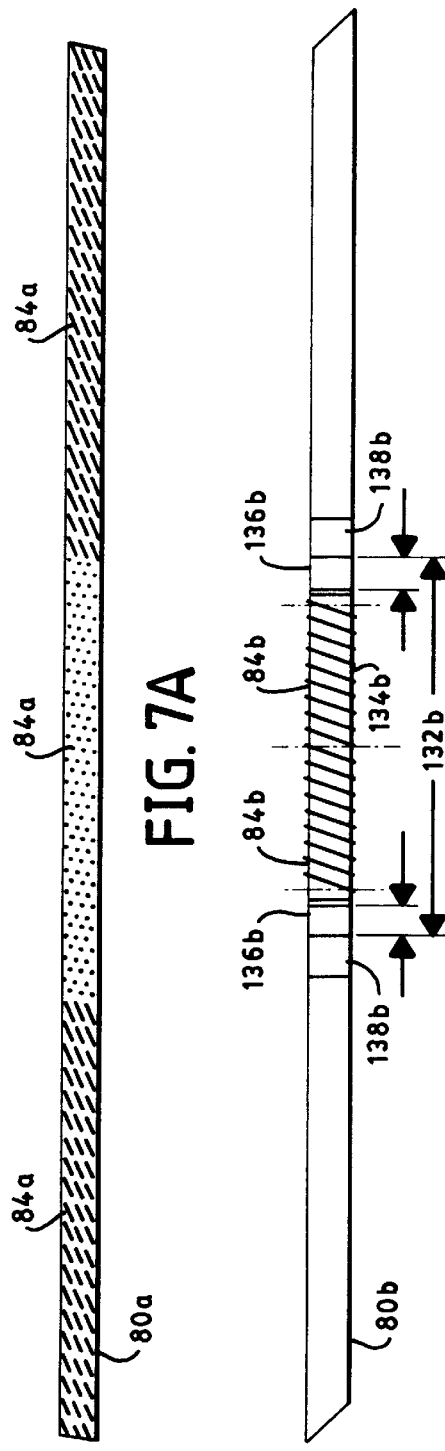

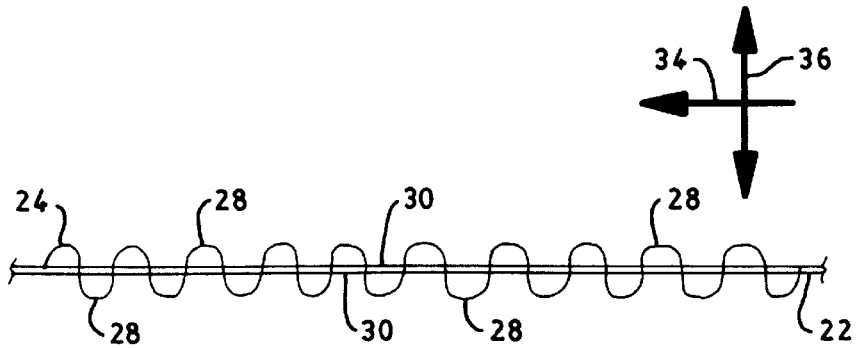
FIG. 12A
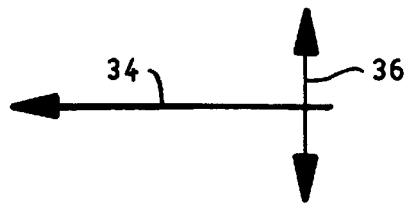
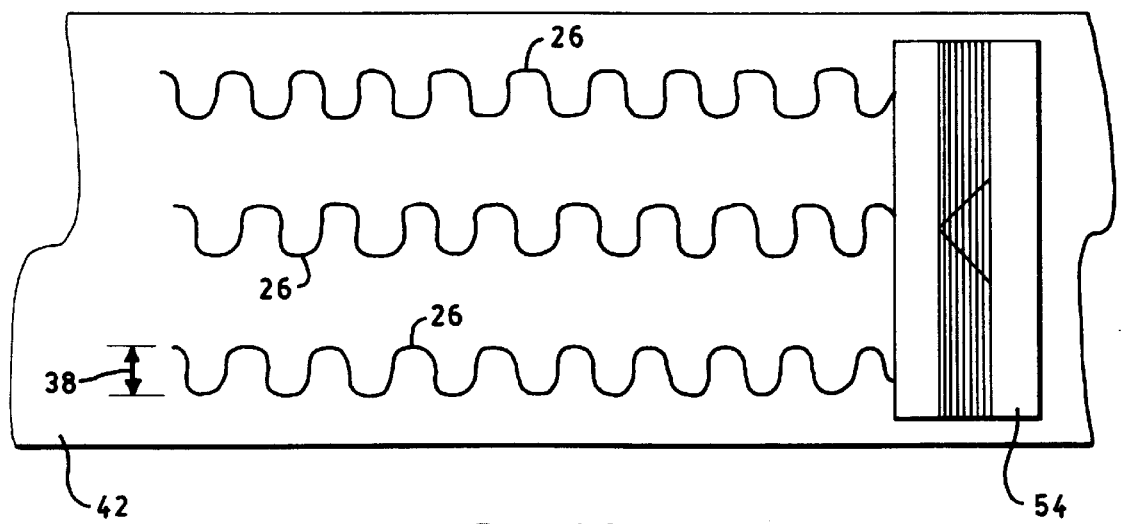
FIG. 12

PROCESS FOR MANUFACTURING AN ELASTIC ARTICLE

This application claims priority from presently copending U.S. Provisional Application No. 60/131,773 entitled "Process for Manufacturing an Elastic Article" and filed on Apr. 30, 1999, in the name of David James Van Eperen, Mark John Beitz, Joseph Conrad Burriss, Robert Thomas Cimini, Chris Lee Heikkinen, Daniel Hoo, David Andrae Justmann, Richard Francis Keller, Douglas Paul Rammer, Lorry Francis Sallee, Jeffrey Joseph Samida, Donald LeRoy Smith, Raymond Gerard St. Louis, Barbara Jean Wink; and U.S. Provisional Application No. 60/095,499 entitled "Absorbent Article With More Conformable Elastics" and filed on Aug. 6, 1998, in the name of Mark John Beitz, Monica Lynn Bontrager, Barbara Ann Gossen, Chris Lee Heikkinen, Daniel Hoo, David Andrae Justmann, Richard Francis Keller, Cynthia Helen Nordness, Douglas Paul Rammer, Lorry Francis Sallee, Raymond Gerard St. Louis, David James VanEperen, Cynthia Louise Wyngaard, Sandra Marie Yarbrough, Roxanne Marie Zuleger, Steven Scott Friderich, Eric Scott Kepner, Kuo-Shu Edward Chang.

FIELD OF THE INVENTION

The present invention relates to an apparatus and process for manufacturing an article which includes strands of material. More particularly, the present invention relates to a manufacturing apparatus and process which can provide a selected system of operations on the strands to provide desired characteristics.

BACKGROUND OF THE INVENTION

Bonding mechanisms have been widely employed to assemble components to form various types of manufactured articles. In particular, adhesives and sonic bonds have been employed to attach components, such as elastomeric members, in disposable articles. Such disposable articles have included absorbent articles, such as disposable diapers, feminine care products, children's training pants, adult incontinence products and the like.

Spray applicators have employed selected air streams to deposit adhesive onto selected components, such as elastic strands. Known techniques have sprayed adhesive onto moving elastic strands held at a distance above a substrate. In addition, known techniques have been employed to helically wrap a filament of adhesive around an elastic strand. Other spray applicators have been employed to assemble the various components of a desired product, such as a disposable diaper. The spray applicators have, for example, been configured to form spiraling spray patterns, swirling spray patterns, and other back-and-forth spray patterns.

In various products, elastic strands have been laminated between layers of polymer film and/or layers of woven or nonwoven fabrics to provide elasticized regions. Folded-over layers have also been employed to enclose or envelop selected strands of material. For example, the folded-over layers have been employed to enclose elastomeric strands within the waistband, leg cuff and inner barrier cuff components of disposable diapers and other disposable absorbent articles.

Conventional adhesive bonding techniques and conventional forming techniques, such as those described above, have shown a need for further improvement. Conventional spray applicators, for example, have exhibited an excessive blow-by of the adhesive, and have not adequately provided a desired combination of secure bonding, creep resistance and low interference with the stretching and retracting properties of adhered elastomeric strands. Conventional forming techniques have not exhibited desired levels of efficiency and effectiveness when producing desired components and component laminates. Additionally, the conventional techniques have not adequately provided components having desired combinations of flexibility and leakage resistance. As a result, there remains a need for improved methods for forming desired assemblies and for adhering components, such as elastomeric components, into an assembled article.

BRIEF DESCRIPTION OF THE INVENTION

Generally stated, the present invention can provide a method for forming an article which includes a strand of material. In particular aspects, at least one first strand of material is moved along an appointed machine-direction. The at least one first strand of material is attached to a substrate, such as a base layer of material, to provide a substrate composite, and a laminate layer can be placed adjacent the at least one first strand of material. At least one second strand of material can be moved along its appointed machine-direction, and the at least one second strand of material can be attached to the base layer. A portion of the base layer can be folded to substantially enclose the at least one first strand and the laminate layer. Alternatively or additionally, a portion of the base layer can be folded to substantially enclose the at least one second strand with the base layer material.

A particular aspect of the invention can include a dividing of at least one of the strands of material into a plurality of strand segments. The dividing can provide a substantially nongathering section of the at least one of the strands, and can provide a substantially nongathering section of the laminate composite.

In another aspect of the invention, the at least one first strand of material can be moved along its appointed machine-direction, and attached to the base layer of material to provide the substrate composite. The laminate layer can be placed onto the at least one first strand of material, and at least one third strand of material can be moved along its appointed machine-direction, and can be attached to the laminate layer. An appointed portion of the base layer can be folded to substantially enclose the at least one first strand, the laminate layer and the at least one third strand with the base layer material.

A further aspect the invention can provide a method and apparatus for forming an article which includes one or more distinctively configured strands of material. In particular aspects, the invention can provide a method and apparatus for wrapping a strand of material with a selected filament, and the filament can desirably be an adhesive filament. The technique of the invention can include a moving of the strand of material at a selected speed along an appointed machine-direction. A substantially continuous filament can be directed onto the strand of material along an oscillating filament path, and the filament can provide a plurality of filament threads disposed at opposed, lateral side regions of the strand of material. Additionally, an air stream can be directed to operatively wrap the filament threads around the strand of material.

In its various aspects, the present invention can more effectively and efficiently produce an article which includes one or more strands of material. Where, for example, the technique of the invention is configured to include the dividing of at least one elastomeric strand of material into a plurality of strand segments, the technique of the invention can provide a substantially nongathering section of the at least one strand, and can provide a substantially nongathering section of the substrate composite or laminate composite. The laminate composite can provide a more effective component which can be advantageously configured to generate improved gasketing and improved fit. Where the technique of the invention is configured to wrap a material strand with an adhesive filament, the technique can exhibit less blow-by of the adhesive, help reduce cost and can provide a desired combination of secure bonding and creep resistance. Where the technique is configured to wrap an elastomeric strand, the technique can provide a low interference with the stretching and retracting properties of the elastomeric strands. When products incorporate the articles or components that are produced in accordance with the present invention, the products can advantageously exhibit improved combinations of fit, flexibility, comfort and leakage resistance.

BRIEF DESCRIPTION OF THE DRAWINGS

The present invention will be more fully understood and further advantages will become apparent when reference is made to the following detailed description of the invention and the drawings, in which:

FIG. 3A representatively shows an expanded schematic, cross-sectional view through the web illustrated in FIG. 3.

FIG. 4A representatively shows an expanded schematic, cross-sectional view through the web illustrated in FIG. 4.

FIG. 7 representatively shows a top, flat lay-out view of the portion of the operating surface of the rotary anvil illustrated in FIG. 6;

FIG. 7A representatively shows a top, flat lay-out view of the portion of the operating surface of the rotary anvil illustrated in FIG. 6B;

FIG. 7B representatively shows a top, flat lay-out view of the portion of the operating surface of the rotary anvil illustrated in FIG. 6D;

FIG. 12 representatively shows a schematic, top view of a reciprocating pattern in each of a plurality of adhesive filaments delivered from the applicator;

FIG. 12A representatively shows a schematic, top view of the reciprocating pattern of the adhesive filament applied onto its appointed strand of material.

DETAILED DESCRIPTION OF THE INVENTION

The present invention can provide an improved method and apparatus for forming an article which includes one or more distinctively configured strands of material. In particular aspects, the invention can provide a method and apparatus for wrapping a strand of material with a selected filament. The invention can be employed to form assembled structures in personal care products, such as diapers, feminine care products, children's training pants, adult incontinence products and the like.

Figure 1:
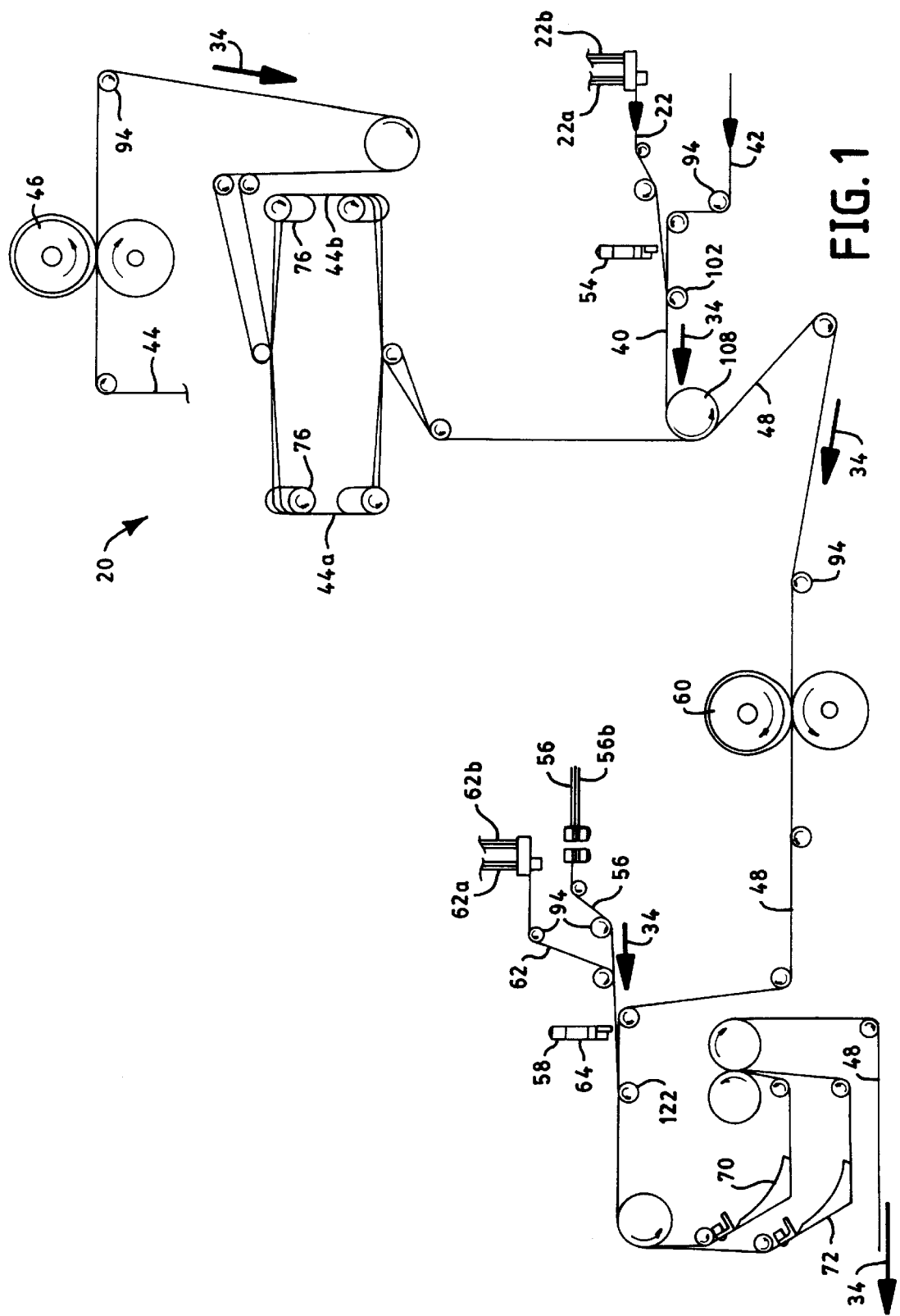
FIG. 1 representatively shows a schematic, side view of a method and apparatus for forming and assembling an elasticized component.
Figure 1A:
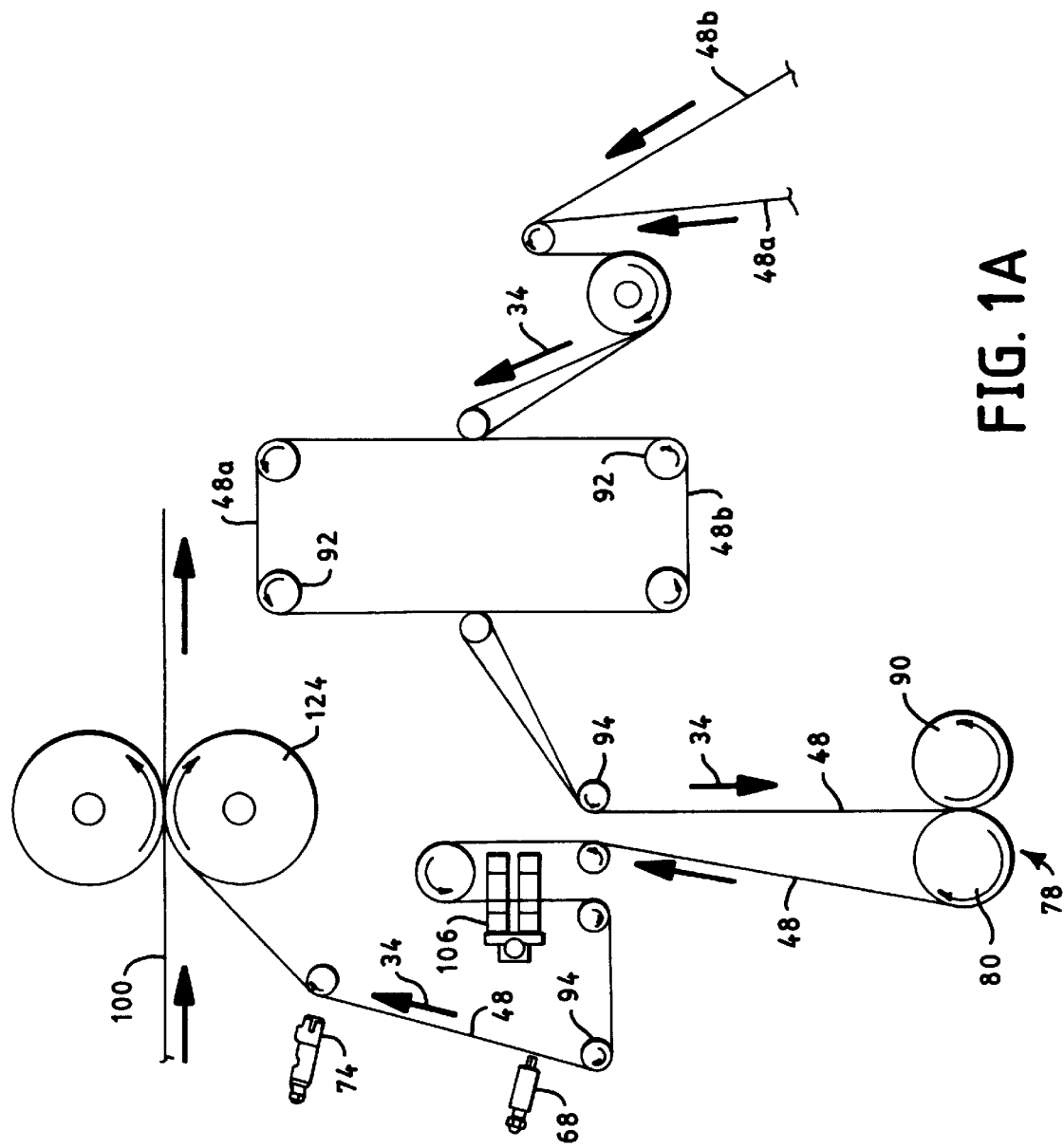
FIG. 1A representatively shows a schematic, side view of a method and apparatus for further forming the elasticized component and assembling the component into a product article.

It should also be noted that, when employed in the present disclosure, the terms "comprises", "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. With reference to FIGS. 1 and 1A, the invention can provide a method and apparatus for forming an article which includes one or more strands of material. For example, the technique of the invention may be employed to form a gusset-flap components which is constructed to provide a combination, elasticized leg gather and elasticized inner containment flap of a disposable diaper. Examples of such diapers are described in U.S. patent application Ser. No. 954,400 entitled ABSORBENT ARTICLE WITH ENHANCED ELASTIC DESIGN FOR IMPROVED AESTHETICS AND CONTAINMENT by R. St. Louis et al. and filed Oct. 20, 1997 which issued as U.S. Pat. No. 5,993,433 on Nov. 30, 1999; and in U.S. patent application Ser. No. 09/327,368 entitled ABSORBENT ARTICLE WITH MORE CONFORMABLE ELASTICS by M. Beitz et al. and filed June. 4, 1999. The entire disclosures of these documents are incorporated herein by reference in a manner that is consistent herewith.

Figure 2:
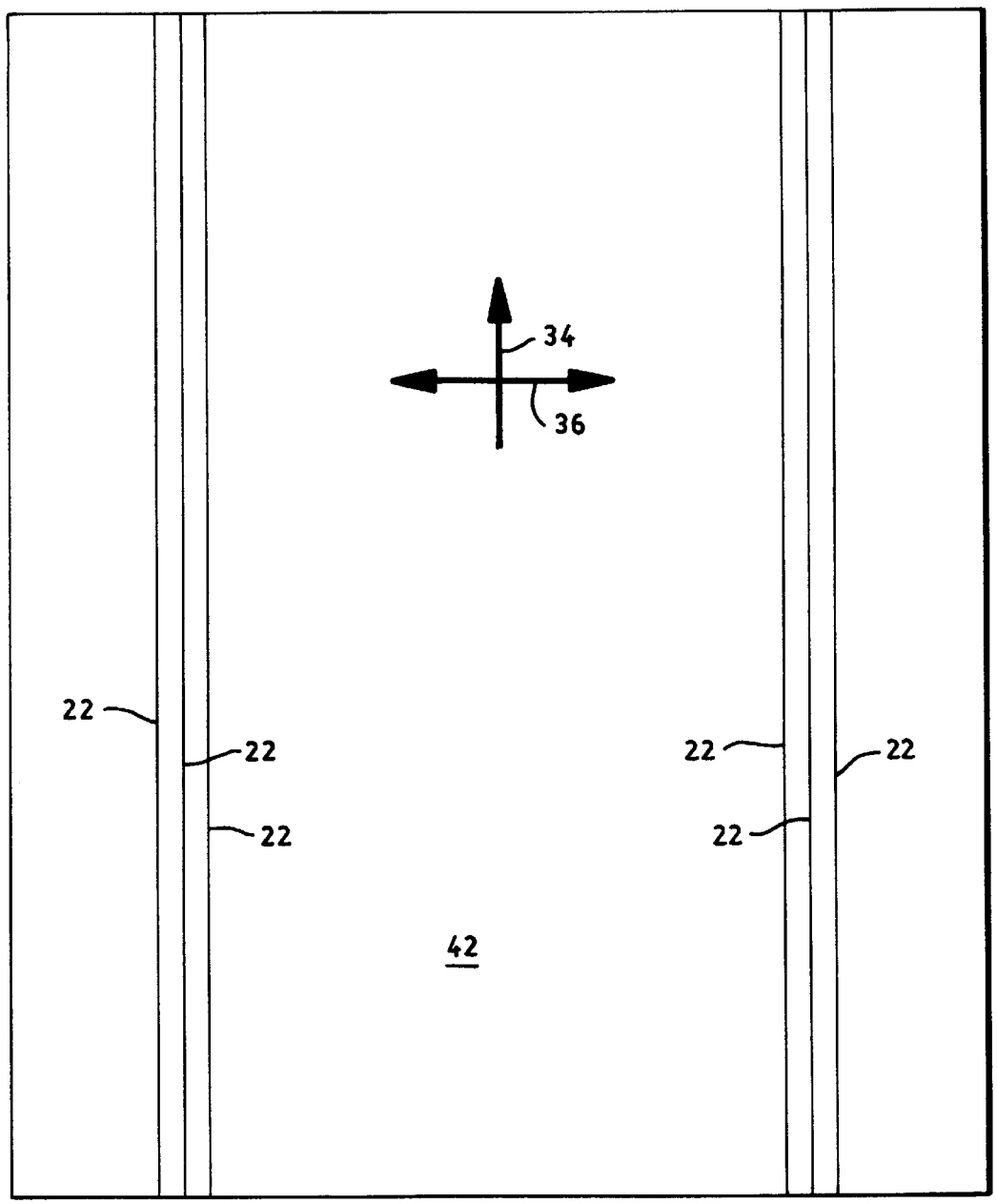
FIG. 2 representatively shows a schematic, top view of a component having a first set of strands assembled to a base, substrate layer to provide a substrate composite web.

The process and apparatus of the invention can have an appointed machine-direction 34 (e.g. FIG. 1) and an appointed cross-direction 36 (e.g. FIG. 2). For the purposes of the present invention, the machine-direction 34 is the longitudinal direction along which a particular component or material is transported length-wise along and through a particular, local position of the apparatus and method of the invention. The cross-direction 36 lies generally within the plane of the material being transported through the process and is aligned perpendicular to the local machine-direction 34. Accordingly, in the view of the arrangement representatively shown in FIG. 1, the cross-direction 36 extends perpendicular to the plane of the sheet of the drawing.

In the present invention, at least one first strand of material, such as a strand 22, can be moved along its appointed machine-direction 34. The at least one first strand of material can be attached to an appointed substrate, such as the representatively shown base layer of material 42, to provide a substrate composite 40. Additionally, a laminate layer 44 can be placed operatively adjacent to the at least one first strand of material to provide a laminate composite web 48. The laminate layer 44 can, for example, be placed onto and joined to the at least one first strand 22 of material to provide the laminate composite web. In particular aspects, the technique of the invention can place a major facing surface of the laminate layer in contact with the first strands 22. In another aspect, at least one second strand of material, such as a strand 56, can be moved along its appointed machine-direction, and the at least one second strand of material can be attached to the base layer 42. In a further aspect, an appointed first portion of the base layer 42 can be folded to substantially enclose the at least one second strand 56 with the base layer material (e.g. FIG. 5). Alternatively or additionally, an appointed second portion of the base layer 42 can be folded to substantially enclose the at least one first strand 22 and the laminate layer 44 with the base layer material.

In another aspect, the at least one first strand of material, such as the strand 22, can be moved along its appointed machine-direction 34, and can become attached to the base layer of material 42 to provide the substrate composite 40. Additionally, the laminate layer 44 can be placed onto the at least one first strand of material to provide the laminate composite 48. At least one third strand of material, such as a strand 62, can be moved along its appointed machine-direction to become attached to the laminate layer 44. An appointed portion of the base layer 42 can then be folded to substantially enclose the at least one first strand 22, the laminate layer 44 and the at least one third strand 62 with the base layer material.

Still further aspects of the invention can include a dividing of at least one of the various strands of material (e.g. the material strands 22, 56 and/or 62) into a selected plurality of strand segments 126 to provide a substantially nongathering section 98 (e.g. FIG. 8) of at least one of the various strands. In desired configurations, the dividing of the strands can include an ultrasonic dividing operation.

An additional aspect can include a bonding of at least one of the various divided strands of material adjacent at least one longitudinal end of the substantially nongathering section 98. Desirably, the bonding of the at least one, divided strand can include an ultrasonic bonding. In another aspect, the invention can include an attaching of the substrate composite 40 or laminate composite 48 to an appointed product web 100.

Yet another aspect of the invention can include a wrapping of at least one strand of material with a selected filament, and the filament can desirably be an adhesive filament. The technique of the invention can include a moving of a strand of material 22 at a selected speed along an appointed machine-direction 34. In a particular aspect, a substantially continuous filament 24 can be directed onto the strand of material 22 along an oscillating filament path 26 to form a plurality of filament threads 28 extending from opposed lateral side regions 30 of the strand of material 22. In another aspect, an air stream 32 can be directed to operatively wrap the filament threads 28 around the strand of material 22.

The various aspects of the invention, alone and in combination, can advantageously improve the attachment between the material strands and their appointed substrate or laminate layers. The particular operating parameters of the method and apparatus can provide a more effective and more efficient securement between the material strands and their attached layers. In addition, the various aspects and parameters can reduce the amounts of adhesive needed to provide bonding strengths and can help reduce manufacturing costs. Where the material strands are composed of an elastomeric material, for example, the resulting attachment can provide less creeping between the strands and their attached substrate. Where the technique of the invention includes a dividing or chopper mechanism which segments the strands of material in the substrate composite 40 or composite laminate 48, the resulting segmented regions of the elastomeric strands can exhibit less contraction, and can leave desired portions of the article substantially ungathered by the elastomeric strands. Where the technique of the invention includes a bonding of at least one of the various divided strands of material adjacent at least one longitudinal end of the substantially nongathering section of the composite 40 or composite laminate, the bonded elastomeric strands can advantageously exhibit less "snap-back" and can provide a more effective operation.

As illustrated in FIGS. 1 and 1A, at least one first strand of material 22 can be substantially continuously provided from a suitable supply source. In the representatively shown configuration, the supply source can provide a first plurality of substantially continuous material strands 22. The material strands can be composed of any desired material. In the representatively shown arrangement, the material strands are composed of an elastomeric material, and may be appointed to provide leg elastics in a gusset-flap component of a disposable absorbent article, such as a disposable diaper. The elastomeric material may be stretched to a desired elongation, such as an elongation within a range of about 50–400% elongation. Desirably, the stretching is conducted prior to delivering the material strands to the location of a first assembly system, such as a system which includes the representatively shown assembly roller 102. An operative, conventional conveying mechanism, such as the illustrated system of transport rollers 94, can move the strands of material 22 at an operative speed along their appointed machine-direction. In the representatively shown configuration, the technique is arranged to move and group the strands 22 to provide a primary set of strands 22a and a complementary set of strands 22b.

A substantially continuous substrate layer, such as the representatively shown base layer web 42, is provided along its appointed machine-direction, and the transport rollers 94 of the conveying system can be employed to direct the base layer 42 to the appointed first assembly mechanism which is representatively provided by the assembly roller 102. The appointed substrate, base layer web 42, can be composed of any suitable material. For example, the substrate may include a sheet layer, a polymer film, a woven fabric, a nonwoven fabric, or the like, as well as combinations thereof. In the shown configuration, for example, the base layer 42 can be a web composed of a non-woven fabric, such as a spunbond fabric composed of polyolefin fibers.

A first applicator 54 can direct and deposit a selected material onto the individual strands of material 22 in a desired distribution pattern. In the representatively shown arrangement, for example, the deposited material can be an adhesive, such as a hot-melt, pressure-sensitive adhesive, and the adhesive can be provided in the form of individual filaments 24. The selected distribution pattern can, for example, be generated by directing each adhesive filament along an individual, oscillating filament path 26, and depositing at least one individual adhesive filament onto each strand of material. In desired arrangements, the adhesive filament can be operatively wrapped around its corresponding strand of material. For example, an individual, substantially continuous first filament of adhesive 24 can be directed onto each first strand of material 22 along an individual oscillating filament path 26. Each first filament of adhesive can be arranged to form a first plurality of filament arches disposed from each lateral side region of their corresponding first strand of material. At least one first air stream can be directed to operatively wrap a substantial majority of the first filament arches around their corresponding strand of material, and the at least one first strand of material and wrapped adhesive can be placed onto the appointed substrate, base layer 42.

In the illustrated configuration, for example, the technique of the invention can provide six individual strands 22, and the strands can be segregated into desired groupings of strands, such as the two sets of strands 22a and 22b which include three strands in each set. The first applicator 54 can be constructed to provide six individual applicator nozzles 104 to deliver a corresponding, individual adhesive filament 24 onto each of the strands 22.

The material strands 22 and the base layer web 42 are operatively directed and transported to a first assembly system, such as a system which includes the representatively shown assembly roll 102. At the assembly roller, the material strands and their applied adhesive are contacted onto the substrate, base web 42 to form the substrate composite 40. An example of a representative substrate composite is illustrated in FIG. 2. The assembled substrate composite can then be directed and transported to an appointed second assembly system, such as a system which includes the illustrated assembly roller 108.

A substantially continuous laminate layer web 44 can be delivered from a suitable supply source, and the representative transport rollers 94 of the conveying system can direct the laminate web 44 through the method and apparatus of the invention. As representatively shown, a suitable dividing device, such as the illustrated rotary slitter 46, may be employed to separate the laminate web 44 into a first laminate web section 44a and a second laminate web section 44b. The conveying system can also include a conventional first web guiding mechanism 76 to direct the laminate layer sections 44a and 44b to the second assembly roller 108. For example a suitable guiding device can be a FIFE guide available from FIFE Corporation, a business having offices located in Oklahoma City, Okla.

The laminate layer web material can be composed of any suitable material. For example, the substrate may include a sheet layer, a polymer film, a woven fabric, a nonwoven fabric, or the like, as well as combinations thereof. In the shown configuration, for example, the laminate web layer may be composed of a substantially liquid impermeable polymer film.

Figure 3:
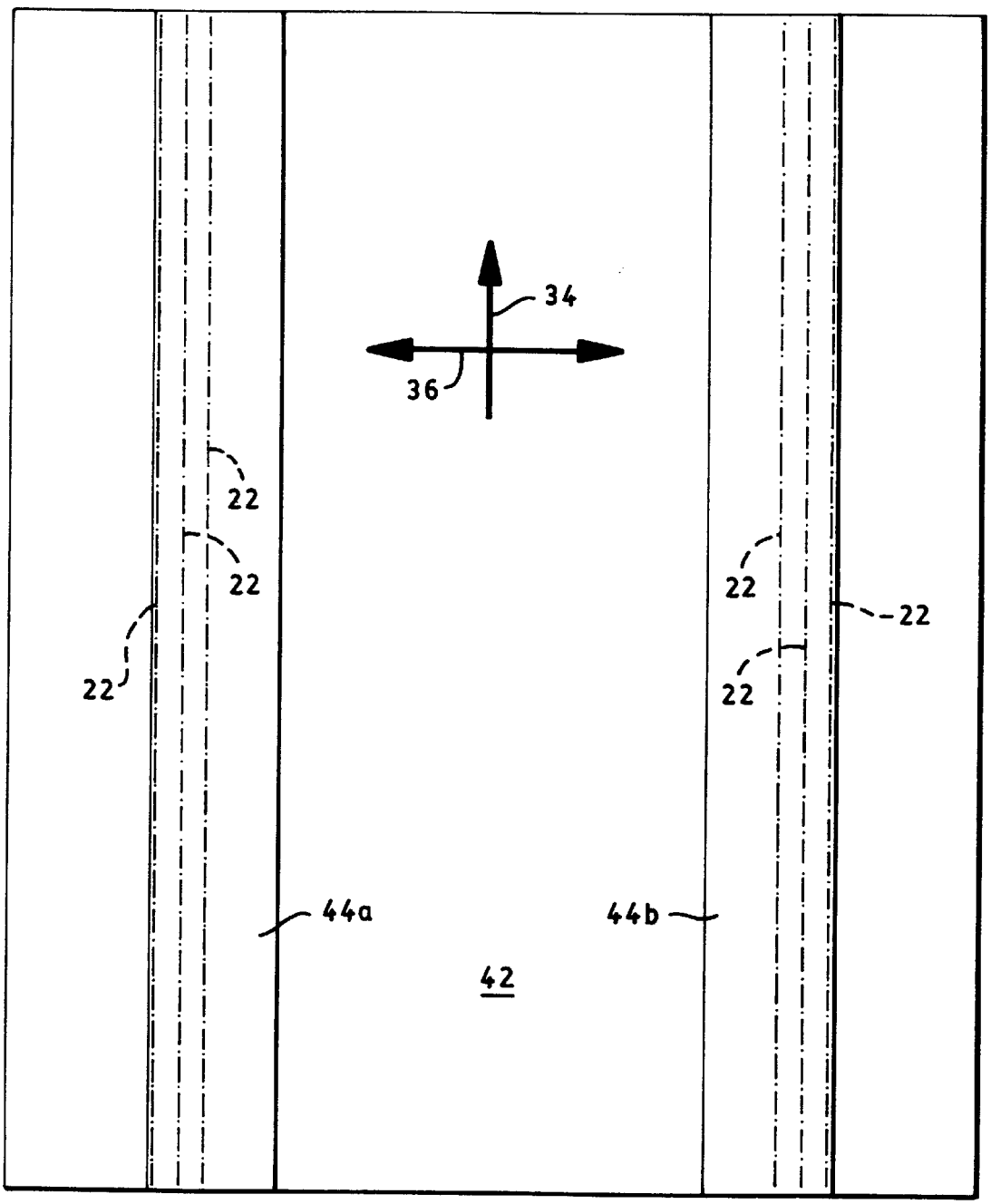
FIG. 3 representatively shows a schematic, top view of laminate layer assembled to a substrate composite to provide a laminate composite web.

With reference to FIGS. 1 and 3, the laminate layer web 44 can be operatively joined and assembled to the substrate composite 40 at the second assembly roller 108. The laminate layer 44 can be located in a facing relation with the base layer 42, and placed onto and attached to the strands of material 22 to form the laminate composite web 48. In the shown arrangement, the laminate layer section 44a is placed onto and attached to the set of material strands 22a, and the laminate layer section 44b is placed onto and attached to the set of material strands 22b. With reference to FIG. 3A, each of the laminate web sections 44a and 44b has a corresponding laminate web first surface 110 and a laminate web second surface 112. The first surface 110 of each laminate web section 44a and 44b is placed in contact with its corresponding set of first strands 22a and 22b, respectively. In particular, the first surface 110 of each laminate web section can be positioned adjacent to its corresponding set of strands 22a or 22b, and can also be positioned adjacent to a first major facing surface 114 of the base layer web 42. Accordingly, the strands can be sandwiched between the base layer web and the laminate web.

Figure 4:
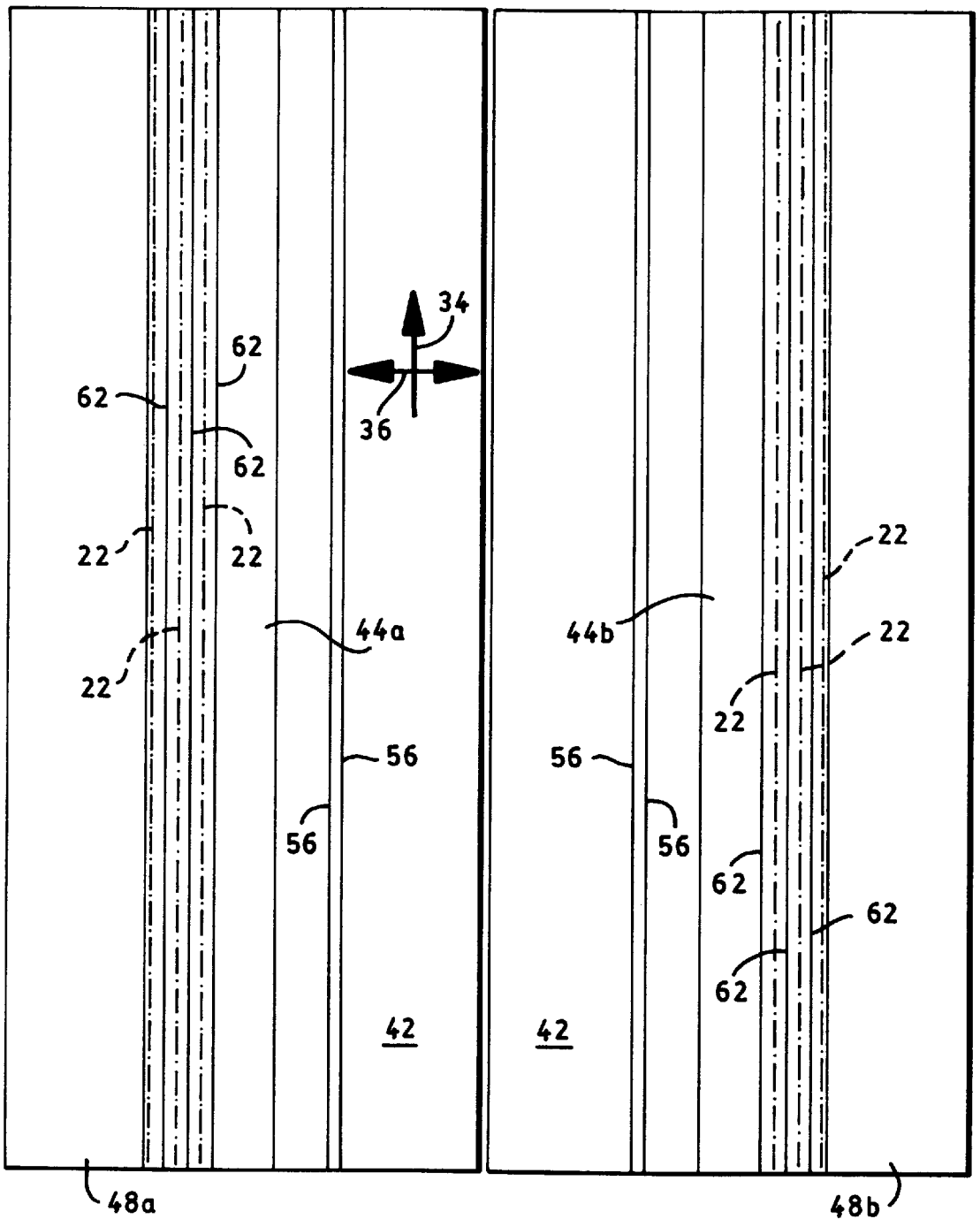
FIG. 4 representatively shows a schematic, top view of a second set of strands and a third set of strands assembled to a laminate composite web.

The conveying system of the invention may direct the laminate composite web 48 to a second cutting mechanism, such as a mechanism which includes the shown rotary slitter 60. With reference to FIGS. 1 and 4, the slitter can operatively separate the laminate composite 48 into a desired number of sections, such as the representatively shown sections 48a and 48b. The conveying system of the invention can then direct the laminate composite web 48 toward a third assembly mechanism, such as a mechanism which includes the illustrated assembly roller 122.

In a further aspect of the invention, at least one second strand of material 56 can be delivered from a conventional supply source. As illustrated, for example, a plurality of the second material strands 56 can be supplied and operatively grouped to provide a primary set of strands 56a and complementary set of strands 56b. The second material strands can be composed of any desired material. In the representatively shown arrangement, the second material strands are composed of an elastomeric material, and may be appointed to provide containment-flap elastics in the gusset-flap component of a disposable absorbent article, such as a disposable diaper. The elastomeric material may be stretched to a desired elongation, such as an elongation within a range of about 50–400% elongation. Desirably, the stretching is conducted prior to delivering the second material strands to the location of the third assembly roller 122.

With reference to FIGS. 4 and 4A, each of the sets of the second material strands 56 can be delivered for positioning onto a selected region of the laminate composite web 48. In the shown arrangement, for example, each of the sets of the second material strands 56 can be placed onto a selected portion of the base layer web 42. For example, the primary set 56a of the second material strands 56 can be placed onto an appointed section of the base layer web material 42 in the first section 48a of the laminate composite web 48, and the complementary set 56b of the second material strands can be placed onto an appointed section of the base layer web material 42 in the second section 48b of the laminate composite web. A second applicator 58 can be employed to adhesively attach the second material strands 56 onto the laminate composite web 48. It should be readily appreciated that the applicating system at the location of the second applicator 58 can be constructed and arranged with a configuration which is similar to the applicator system provided at the location of the first applicator 54.

Accordingly, the second applicator 58 can direct and deposit a selected material onto the individual strands of material 56 in a desired distribution pattern. In the representatively shown arrangement, for example, the deposited material can be an adhesive, such as a hot-melt, pressure-sensitive adhesive, and the adhesive can be provided in the form of individual filaments 24. The selected distribution pattern can, for example, be generated by directing each adhesive filament along an individual, oscillating filament path 26, and depositing at least one individual adhesive filament onto each strand of material. In desired arrangements, the adhesive filament can be operatively wrapped around its corresponding strand of material. For example, an individual, substantially continuous second filament adhesive can be directed onto each second strand of material 56 along an individual oscillating filament path. Each second filament of adhesive can be arranged to form a second plurality of filament arches extending from each lateral side of their corresponding strand of material 56. At least one second air stream can be directed to operatively wrap a substantial majority of the second filament arches around their corresponding strand of material, and the at least one second strand of material and wrapped adhesive can be placed onto the substrate, base layer 42.

In the illustrated configuration, for example, the technique of the invention can provide four individual strands 56, and the strands can be segregated into desired groupings of strands, such as the two sets of strands 56a and 56b which include two strands in each set. The second applicator 58 can be constructed to provide four individual applicator nozzles 104 to deliver a corresponding, individual adhesive filament 24 onto each of the strands 56.

In an additional aspect of the invention, at least one third strand of material 62 can be provided from a suitable supply source and delivered into the technique of the invention. In the shown configuration, for example, the technique is arranged to provide a plurality of third material strands 62, and the third strands are grouped to provide a primary set of material strands 62a and a complementary set of material strands 62b. The third material strands can be composed of any desired material. In the representatively shown arrangement, the third material strands are composed of an elastomeric material, and may be appointed to provide supplemental leg elastics in the gusset-flap component of a disposable absorbent article, such as a disposable diaper. The third material strands may be stretched to a desired elongation, such as an elongation within a range of about 50–400% elongation. Desirably, the stretching is conducted prior to delivering the material strands to the location of the third assembly roller 122.

The conveying system of the invention is operatively arranged to deliver the third strands of material 62 to the location of the third assembly roller 122 and to a third applicator 64. The third material strands 62 are selectively placed onto an appointed region of the laminate composite web 48. In the illustrated configuration, for example, the third material strand 62 are placed onto a second major facing surface 112 of the laminate layer web material 44. In particular aspects, the primary set 62a of the third material strands can be positioned onto the surface 112 of the first laminate web section 44a, and the complementary set 62b of the third material strands can be positioned onto the surface 112 of the second laminate web section 44b.

The adhesive applicator system provided at the location of the third applicator 64 can be constructed and arranged with a configuration that is similar to the configuration of the applicator system constructed at the location of the first applicator 54. Accordingly, the third applicator 64 can direct and deposit a selected material onto the individual strands of material 62 in a desired distribution pattern. In the representatively shown arrangement, for example, the deposited material can be an adhesive, such as a hot-melt, pressure-sensitive adhesive, and the adhesive can be provided in the form of individual filaments 24. The selected distribution pattern can, for example, be generated by directing each adhesive filament along an individual, oscillating filament path 26, and depositing at least one individual adhesive filament onto each strand of material. In desired arrangements, the adhesive filament can be operatively wrapped around its corresponding strand of material. For example, at least one third strand of material 62 can be moved along an appointed machine-direction, and an individual, substantially continuous third filament of adhesive can be directed onto each third strand of material 62 along an oscillating filament path. Each third filament of adhesive can be arranged to form a second plurality of filament arches extending from each lateral side region of their corresponding strand of material 62. At least one third air stream can be directed to operatively wrap a majority of the third filament arches around their corresponding strand of material, and the at least one third strand of material 62 can be placed onto the appointed substrate, laminate composite 48.

In the illustrated configuration, for example, the technique of the invention can provide six individual strands 62, and the strands can be segregated into desired groupings of strands, such as the two sets of strands 62a and 62b which include three strands in each set. The third applicator 64 can be constructed to provide six individual applicator nozzles 104 to deliver a corresponding, individual adhesive filament 24 onto each of the strands 62.

In the various configurations of the invention, the appointed applicator (e.g. applicator 54, 58 and/or 64) may comprise a module which contains the required number of applicator orifices or nozzles 104 for generating the desired number of individual filaments 24. In addition, the various, separately identified applicators may be combined in any desired combination. As representatively shown, for example, the second applicator 58 and the third applicator 64 can be combined into a common module. Suitable applicator modules can include an ITW Uniform Fiber Depositor device, such a model OMEGA UFD incorporating ITW part numbers 105964, 105965 and 105966. Suitable equipment is available from ITW Dynatec, a business having offices in Hendersonville, Tenn.

Figure 5:
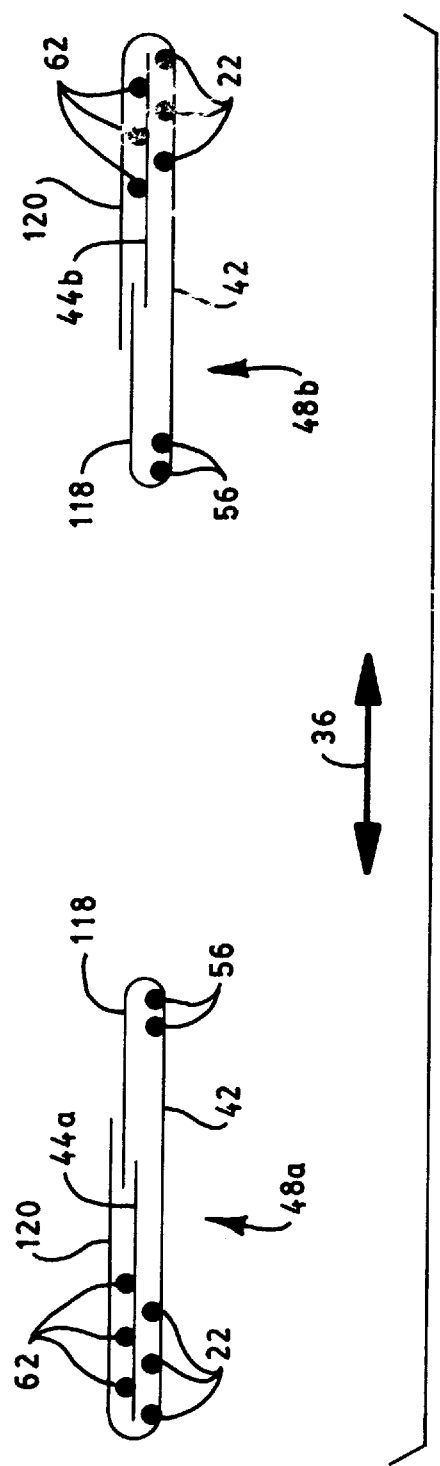
FIG. 5 representatively shows schematic, cross-sectional view in which portions of the base substrate layer are folded over to enclose the laminate layer and strand components of the laminate composite web.

In further aspects of the invention, the conveying system of the invention can direct the laminate composite web 48 to an operative folding mechanism, such as an air-jet folding system, a system of folding rollers or a system of folding boards. With reference to FIGS. 1 and 5, for example, an arrangement of first folding boards 70 can be configured to generate a first folded portion of the base layer web 42. The first folding boards can, for example, be configured to place a folded, containment-flap portion 118 of the base layer web 42 onto the second material strands 56 to substantially enclose the second material strands with the base layer web. In the illustrated configuration, the first folded portion 118 of the base web material in the first section 48a of the laminate composite is positioned over and onto the primary set 56a of the second material strands. Similarly, the first folded portion 118 of the base web material in the second laminate section 48b of the laminate composite web can be positioned over and onto the complementary set 56b of the second material strands.

In other aspects, an arrangement of second folding boards 72 can be configured to form a second folded portion of the base layer web 42. The second folding boards can, for example, be configured to place a folded, leg-gusset portion 120 of the base layer web 42 in a position which is at least over the first material strands 22 to substantially enclose the first material strands with the base layer web. In the representatively shown configuration, the second folded portion 120 of the base web material in the first section 48a of the laminate composite is positioned over the primary set 22a of the third material strands. Similarly, the second folded portion 120 of the base web material in the second laminate section 48b of the laminate composite web can be positioned over the complementary set 22b of the first material strands.

In further aspects, the second system of folding boards 72 can be employed to position the folded leg-gusset portion 120 of the base web of material in a superposed position over the first material strands 22, and the laminate layer 44 in the laminate composite web 48. For example, the second folded portion 120 of the base web material in the first section 48a of the laminate composite 48 is superposed over the primary set 22a of the first material strands 22 and the first web section 44a of the laminate web 44 in the first section 48a of the laminate composite 48. Similarly, the second folded portion 120 of the base web material in the second section 48b of the laminate composite 48 can be superposed onto the complementary set 22b of the first material strands 22 and the second section 44b of the laminate web 44 in the second section 48b of the laminate composite.

In the representatively shown arrangement, the second system of folding boards 72 can be employed to position the folded, leg-gusset portion 120 of the base web of material in a superposed position over the first material strands 22, the laminate layer 44 and the third material strands 62 in the laminate composite web 48. In the shown system, for example, the folded, leg-gusset portion 120 of the base web material in the first section 48a of the laminate composite 48 is superposed over the primary set 22a of the first material strands 22, the first web section 44a of the laminate web 44 and the primary set 62a of the third material strands 62 in the first section 48a of the laminate composite 48. Similarly, the folded, leg-gusset portion 120 of the base web material in the second section 48b of the laminate composite 48 can be superposed onto the complementary set 22b of the first material strands 22, the second section 44b of the laminate web 44 and the complementary set 62b of the third material strands 62 in the second section 48b of the laminate composite.

Figure 8:
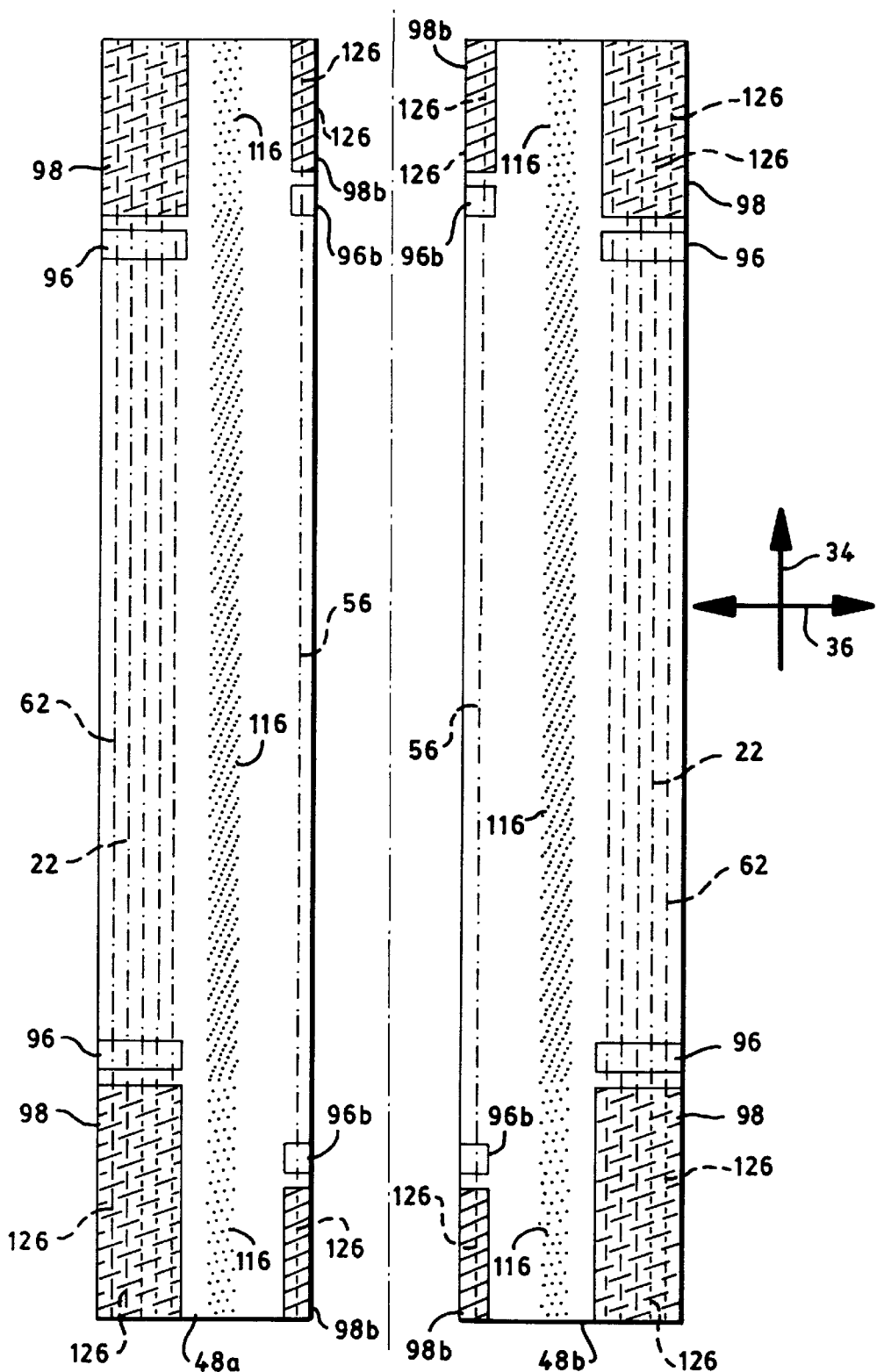
FIG. 8 representatively shows a schematic, top view of a laminate composite web which includes patterns of ultrasonic bonding and cutting, and arrangements of segmented strands.

With reference to FIGS. 1A and 8, the conveying system of the invention and a suitable web guiding mechanism 92 can transport and guide the laminate composite web 48 to a chopper mechanism 78 which operatively divides an appointed, substantially nongathering section 98 of at least one the material strands in the substrate composite 40 or laminate composite 48 to form a plurality of strand segments 126. For example, the chopper mechanism can be configured to divide at least one selected section 98, and desirably a plurality of sections, of the at least one first material strand 22 into a predetermined number of first strand segments. Alternatively or additionally, the chopper mechanism may divide at least one selected section, and desirably a plurality of sections, of the at least one second material strand 56 into a predetermined number of corresponding second strand segments. Similarly, at least one selected section, and desirably a plurality of sections, of the at least one third material strand 62 can be divided into a predetermined number of corresponding third strand segments.

The chopper mechanism 78 may include any operative dividing device, such as a cutting device, a heating device, an ultrasonic device, or the like as well as combinations thereof. In the illustrated arrangement, for example, the chopper mechanism 78 can include an ultrasonic cutter system.

The technique of the invention can also include a bonding mechanism and operation which, for example, may be incorporated to operatively provide an attachment 96 of at least one divided strand (strand 22, 56 and/or 62), and desirably two or more attachments involving a plurality of divided strands, adjacent a longitudinal end of each corresponding, substantially nongathering section 98. The bonding device and operation may be further configured to attach each of the second folded portions 120 of the base web material onto its corresponding portion of the laminate composite 48 to help envelope the first material strands 22 and/or the third material strands 62 within the assembly. Additionally, the bonding operation, for example, may be employed to further attach each of the first folded portions 118 of the base web material onto its corresponding portion of the laminate composite 48 to help envelope the second material strands 56 within the assembly.

In desired arrangements, the bonding of the strands can include an ultrasonic bonding. Additionally, the bonding operation may be conducted in cooperation with the dividing operation. In the shown configurations, for example, the ultrasonic system can provide an ultrasonic bonding operation in cooperation with the ultrasonic dividing operation.

Figure 9:
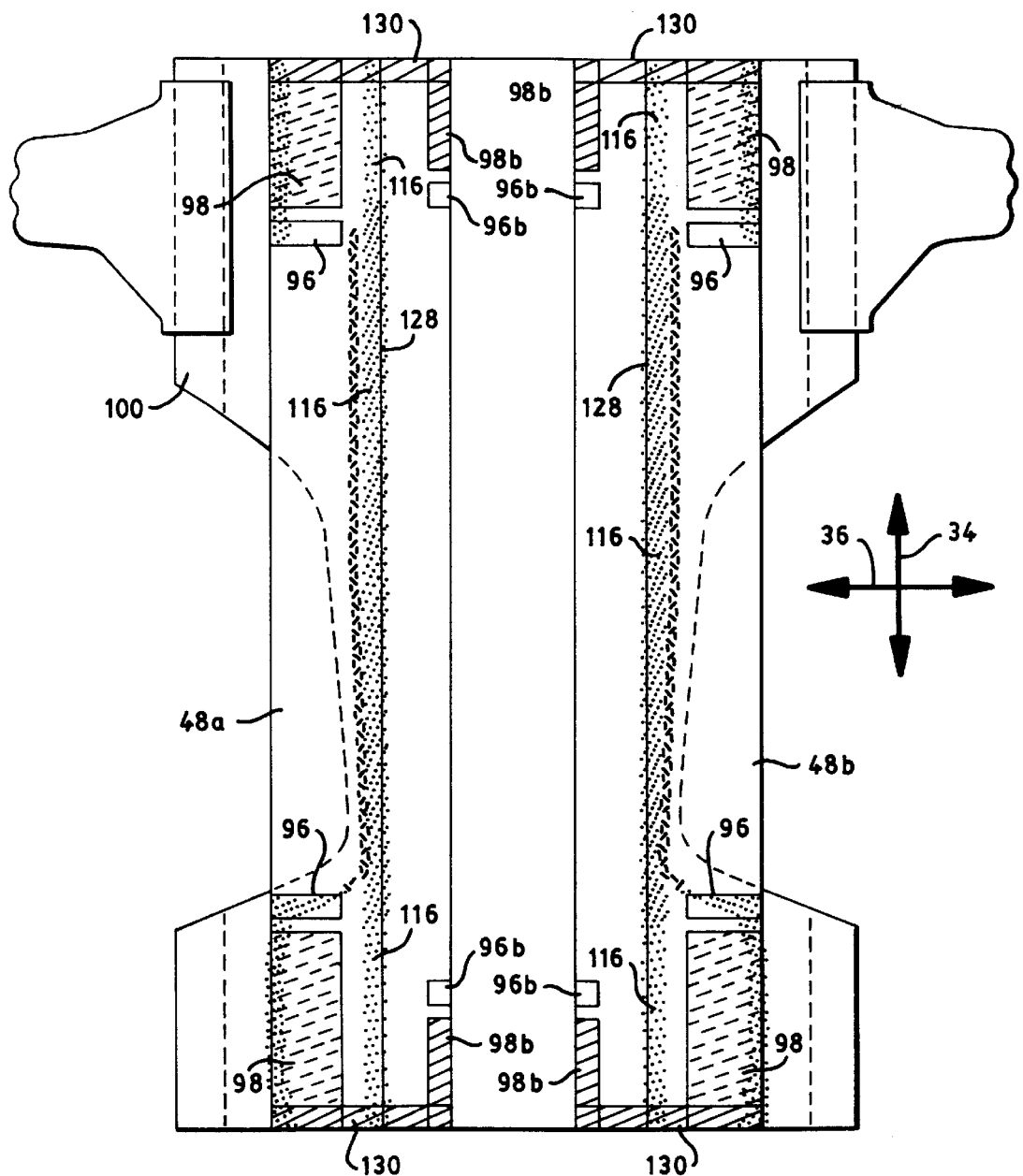
FIG. 9 representatively shows a schematic, plan view of a product web in which each lateral side region of the product web has an attached laminate composite web.

The laminate composite 48 (e.g. the composite sections 48a and 48b) can then be conveyed and guided to a fourth assembly mechanism 124 to attached the laminate composite 48 to a moving product web 100. In particular arrangements, the product web 100 can include a pair of cross-directionally opposed, side edge regions, and one of the laminate composite sections 48a or 48b can be attached to each side edge region of the product web, as representatively shown in FIG. 9.

As representatively shown, for example, the system of transport rollers 94 and a suitable web guiding mechanism 106 can direct the laminate composite 48 to a bonding mechanism which provides a longitudinal attachment between the laminate composite 48 and the product web 100 along the machine-direction of the product web. For example, a fourth adhesive applicator 68 can apply a barrier bead or strip of adhesive at an appointed location along the machine-direction of the laminate composite. Desirably, the fourth applicator 68 is configured to provide a substantially continuous attachment 128 (FIG. 9) between the laminate composite 48 and the product web 100 along the machine-direction of the product web. The barrier attachment 128 may optionally be discontinuous.

In a further aspect, the present invention can include another bonding mechanism which secures discrete, spaced apart sections of the laminate composite 48 to the product web 100. For example, a fifth adhesive applicator 74 can be configured to intermittently apply a pattern of adhesive onto individual spaced apart sections of the laminate composite 48 at appointed regions which are separated along the machine-direction of the laminate composite. Accordingly, the applicator 74 can provide a sequence of end-seal attachments 130 (FIG. 9) between the laminate composite 48 and the product web 100. The end-seal attachments can be spaced apart by a predetermined distance along the machine-direction of the product web.

In alternative configurations, it should be readily apparent that the bonding mechanisms employed with the invention may be of various types. The bonding mechanisms may, for example, provide adhesive bonds, thermal bonds, ultrasonic bonds, stitching, pinning, stapling or the like, as well as combinations thereof.

In the various arrangements of the invention, the selected strands of material (e.g. the strands 22, 56 and/or 62) can have any desired cross-sectional shape. For example, the cross-sectional shape of the strands can be round, oval, rectangle, trapezoidal, irregular, or the like, as well as combinations thereof. Additionally, the appointed strands of material can be composed of any desired material, such as natural rubber, synthetic rubber, polyurethane elastomers, polyisoprene elastomers, styrene-isoprene-styrene block copolymer elastomers, or the like, as well as combinations thereof. In the shown arrangements, the various strands can be composed of an elastomeric material, such as GLOSPAN elastomer (available from Globe Manufacturing Company, a business having offices in Fall River, Mass.), LYCRA elastomer (available from E. I. DuPont de Nemours and Company, a business having offices in Wilmington, Del.), or the like.

Figure 6A:
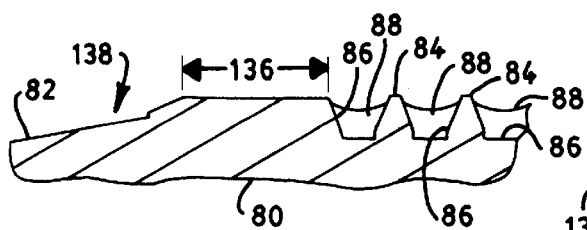
FIG. 6A representatively shows an enlarged cross-sectional view of a portion of the operating surface of the rotary anvil illustrated in FIG. 6.
Figure 6:
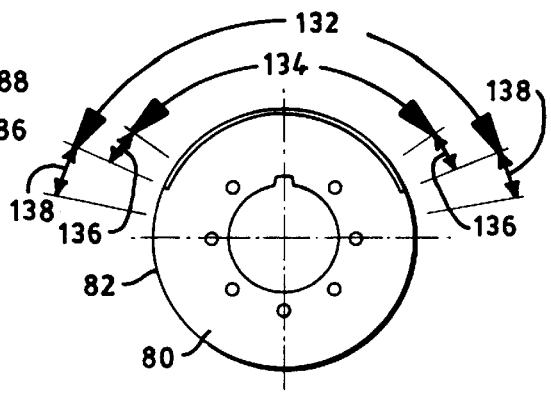
FIG. 6 representatively shows a schematic, side view of a rotary, ultrasonic anvil component which may be employed to form an array of bonds and cut strand segments in the laminate composite web.

With reference to FIGS. 1A and 6, the chopper mechanism and/or bonding mechanism employed with the present invention may be provided by an ultrasonic device having rotary components. For example the device can include a first, rotary anvil device 80, and a second rotary horn device 90 which cooperates with the first rotary component 80. The rotary anvil 80 provides an outer peripheral surface 82 which includes a plurality of raised portions 84 and a plurality of relatively lower, valley portions 86. The raised portions 84 can, for example, be configured as ridges or bars which extend generally along the axial dimension of the rotary anvil 80. The bars may extend substantially parallel to the rotational axis of the rotary anvil, or may be offset at a selected angle relative to the rotational axis. Other configurations and patterns of the raised portions may optionally be employed, as desired. Such configurations can include hatched patterns, wave patterns, chevron patterns, dot patterns, or the like, as well as combinations thereof. The patterns may be arranged with regular or irregular configurations and distributions, as desired.

The raised portions are arranged in a predetermined pattern, and are configured to contact and operate on selected regions of the appointed target material (e.g. the laminate composite 48). For example, the raised portions can be selectively configured to provide a dividing operation. In particular aspects, the raised portions 84 can be constructed to provide a chopper device, wherein the raised portions 84 are configured to cut selected, assembled strands of material at predetermined spaced apart locations to operatively generate the desired plurality and distribution of strand segments 126. In other aspects, the raised portions 84 can be constructed to provide a bonding device, wherein the raised portions 84 are configured to attach and assemble together selected components at predetermined locations.

Where the material strands are composed of an elastomeric material, the segmenting of the strands can operatively disable the elastomeric properties of the strands at the locations in which the strands have been segmented. As a result, the elastomeric strands, can be configured to provide relatively less contraction and gathering at the regions or sections 98 within which the strands have been operatively segmented. It should be readily appreciated that each of the dividing and bonding operations may be accomplished by employing a separate anvil component.

In desired arrangements, selected portions and regions of an integrated, multi-function anvil 80 may be configured to provide different processing operations. For example, the anvil portions can be arranged and distributed sequentially along an axial dimension of the anvil, and the anvil regions can be arranged along a circumferential dimension of the anvil. In a particular aspect, a first portion of the anvil may be configured to include a chopper region which provides a dividing operation with respect to the target material, such as the strands 22 and 62 in an appointed leg-gusset portion of the laminate composite 48. The first anvil portion can also include at least one bonding region which provides a selected securement of the target material (e.g. a securement of selected portions of the strands 22 and 62). In another aspect, a second portion of the anvil may be configured to provide a bonding operation with respect to selected areas of the target material, such as appointed medial portions of the laminate composite 48. In a further aspect, a third portion of the anvil may be configured to include a chopper region which provides a dividing operation with respect to another area of the target material, such as the strands 56 in an appointed containment-flap portion of the laminate composite 48. Additionally, the third anvil portion can be configured to include at least one bonding region which provides another selected securement, such as a securement of particular portions of the strands 56.

With reference to FIGS. 6 and 6A, a first portion of the rotary anvil 80 can have a pattern length 132 which can extend about the anvil along its circumferential dimension, and include an appointed chop area 134. The pattern length may also include one or more selected flat areas 136. In the example of the shown configuration, a flat area is positioned adjacent both of the leading and trailing, circumferential (lengthwise) ends of the chop area 134. Additionally, the first anvil portion may include one or more ramp 20 areas 138. In the shown arrangement, a ramp area is positioned adjacent each flat area 136, with each flat area interposed between its corresponding ramp area and the chop area 134. The chop area 134 can include a first plurality of raised chopper elements or portions 84 which are positioned on the outer peripheral surface of the anvil and distributed along the circumferential length of the chop area 134. As representatively shown in FIGS. 7, for example, the raised portions can have the form of a plurality of linear ridges or bars that generally parallel to one another and are aligned at an angle with respect to the circumferential and axial dimensions of the rotary anvil 80. The raised chopper portions 84 are configured to operatively cut the strands 22 and 62 in their corresponding section of the laminate composite.

Each flat area 136 can be configured to provide a desired bonding operation. With reference to FIG. 8, for example, each flat area can be constructed to attach selected, portions of the base layer 42 to appointed portions of its corresponding strands 22 and 62 and to appointed portions of its corresponding section of the laminate layer 44.

With reference to FIG. 8, the first portion of the anvil 80 can operatively provide a desired pattern array of attachments 96 and cuts which are distributed along the machine-direction and cross-direction 36 of the composite laminate 48. The cuts can operatively deactivate selected sections of the strands to provide the desired, substantially nongathering sections 98 in the composite laminate. The attachments 96 can secure the end portions of the strands that positioned circumferentially adjacent their corresponding, chopped and nongathering sections 98. The strand end portions can be secured to the base layer web 42 and/or laminate layer web 44 to substantially prevent any undesired elastomeric contraction or other "snap-back" of the strand ends. In desired arrangements, for example, the first anvil portion can be employed to provide cuts and bonds to produce substantially nongathering sections in the appointed leg-gusset section of the laminate 48.

Figure 6C:
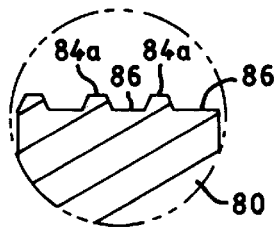
FIG. 6C representatively shows an enlarged cross-sectional view of a bonding surface of the rotary anvil illustrated in FIG. 6B.
Figure 6B:
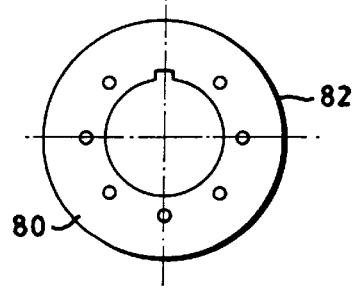
FIG. 6B representatively shows a schematic, side view of a rotary, ultrasonic anvil component which may be employed to form a bond pattern which extends lengthwise along the laminate composite web.

With reference to FIGS. 6B and 6C, a second portion of the rotary anvil 80 can have raised bonding elements or portions 84a located on its outer peripheral surface, and the bonding portions 84a can be distributed lengthwise along a desired portion of the circumferential dimension of the anvil 80. In the representatively shown example, the bonding portions 84a can be distributed substantially continuously along approximately the entire length of the anvil circumference. As representatively shown in FIGS. 7A, for example, the raised portions can have the form of a plurality of dots. The configurations of the individual dots and the dot pattern can be selectively varied along the circumferential length of the second portion of the anvil 80. With reference to FIG. 8, the bonding portions 84a can, for example provide a dot pattern array of sonic bonds 116 which can secure the folded over portions of the base layer to the desired sections of the laminate composite (e.g. the laminate composite sections 48a and 48b).

Figure 6E:
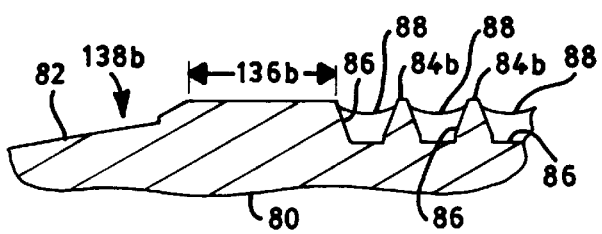
FIG. 6E representatively shows an enlarged cross-sectional view of a portion of the operating surface of the rotary anvil illustrated in FIG. 6D.
Figure 6D:
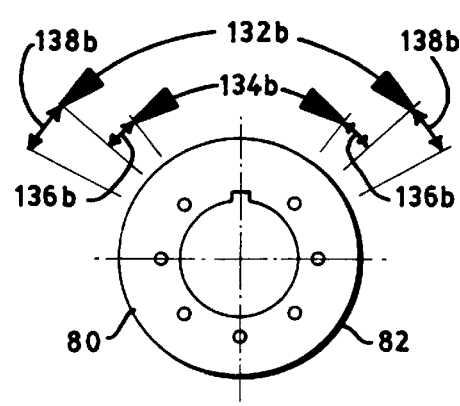
FIG. 6D representatively shows a schematic, side view of a rotary, ultrasonic anvil component which may be employed to form another array of bonds and cut strand segments in the laminate composite web.

With reference to FIGS. 6D and 6E, a third portion of the rotary anvil 80 can have another pattern length 132b which extends about the anvil along its circumferential dimension, and can include another appointed chop area 134b. The pattern length may also include one or more selected flat areas 136b. In the example of the shown configuration, a flat area is positioned adjacent both of the leading and trailing, circumferential (lengthwise) ends of the chop area 134b. Additionally, the third anvil portion may include one or more ramp areas 138b. In the shown arrangement, a ramp area is positioned adjacent each flat area 136b, with each flat area interposed between its corresponding ramp area and the chop area 134b. The chop area 134b can include a corresponding plurality of raised chopper portions 84b which are positioned on the outer peripheral surface of the anvil and distributed along the circumferential length of the chop area 134b. As representatively shown in FIGS. 7B, for example, the raised portions can have the form of a plurality of linear bars that generally parallel to one another and are aligned at an angle with respect to the circumferential dimension of the rotary anvil 80. The raised chopper portions 84b are configured to operatively cut the strands 56 in their corresponding section of the laminate composite.

Each flat area 136b can be configured to provide a desired bonding operation. With reference to FIG. 8, for example, each flat area can be constructed to attach selected, portions of the base layer 42 to appointed portions of its corresponding strands 56 and to appointed portions of its corresponding section of the laminate layer 44.

With reference to FIG. 8, the third portion of the anvil 80 can operatively provide another 15 desired pattern array of attachments 96b and cuts which are distributed along the machine-direction 34 and cross-direction 36 of the composite laminate 48. The cuts can operatively deactivate selected sections of the strands to provide other desired, substantially nongathering sections 98b in the composite laminate. The attachments 96b can secure the end portions of the strands that positioned circumferentially adjacent their corresponding, chopped and nongathering sections 98b. The strand end portions can be secured to the base layer web 42 and/or laminate layer web 44 to substantially prevent any undesired elastomeric contraction or other "snap-back" of the strand ends. In desired arrangements, for example, the third anvil portion can be employed to provide cuts and bonds to produce substantially nongathering sections in the appointed containment-flap section of the laminate 48.

As mentioned in the present description, the flat areas 136 can be positioned at either or both of the leading and trailing edges or their corresponding chop areas 134. Accordingly, the corresponding, bonded attachments 96 can be positioned at either or both of the leading and trailing edges or their corresponding nongathering sections 98. To provide their desired bonding operations, the radially-outermost tops of the flat areas can be constructed to be positioned radially inward from the radially-outermost tops of the raised portions 84. Desirably, the tops of the flat areas can be recessed radially inward from the tops of the raised portions 84 by a distance which is within a range of about 0.001–0.003 inches (0.025–0.076 mm). The flat areas 136 can be recessed radially inward from the outermost surfaces of the raised portions 84 to avoid generating excessive nip forces between the horn and anvil components that could undesirably divide the strands.

The relatively inward, radially lowered portions 86 of the rotary anvil component 80 can include a low-friction or low-adhesion material 88 disposed therein, as illustrated in FIGS. 6A and 6E. Desirably, the low-adhesion material does not readily adhere to the selected adhesives that are employed with the invention. A suitable low-adhesion material include silicone rubber, electroless nickel, polytetrafluoroethylene, chrome, polyurethane, or the like, as well as combinations thereof. In the shown configuration, for example, the low-adhesion material can be a 70 Durometer silicone rubber.

Inserts composed of the silicone rubber can be positioned into selected lower, valley portions 86 of the rotary anvil 80, such as between the raised bar members of the portions of the rotary anvil that are employed to provide the desired chopper mechanisms 78. In the representatively shown arrangement, the outer most peripheral surfaces of the insert are positioned approximately 0.02–0.04 inches (about 0.05–0.1 cm) away from the outer peripheral surfaces of the raised portions 84. Accordingly, the outer most surfaces of the silicone rubber inserts are recessed away from the outer most surface of the raised portions 84.

Figure 10:
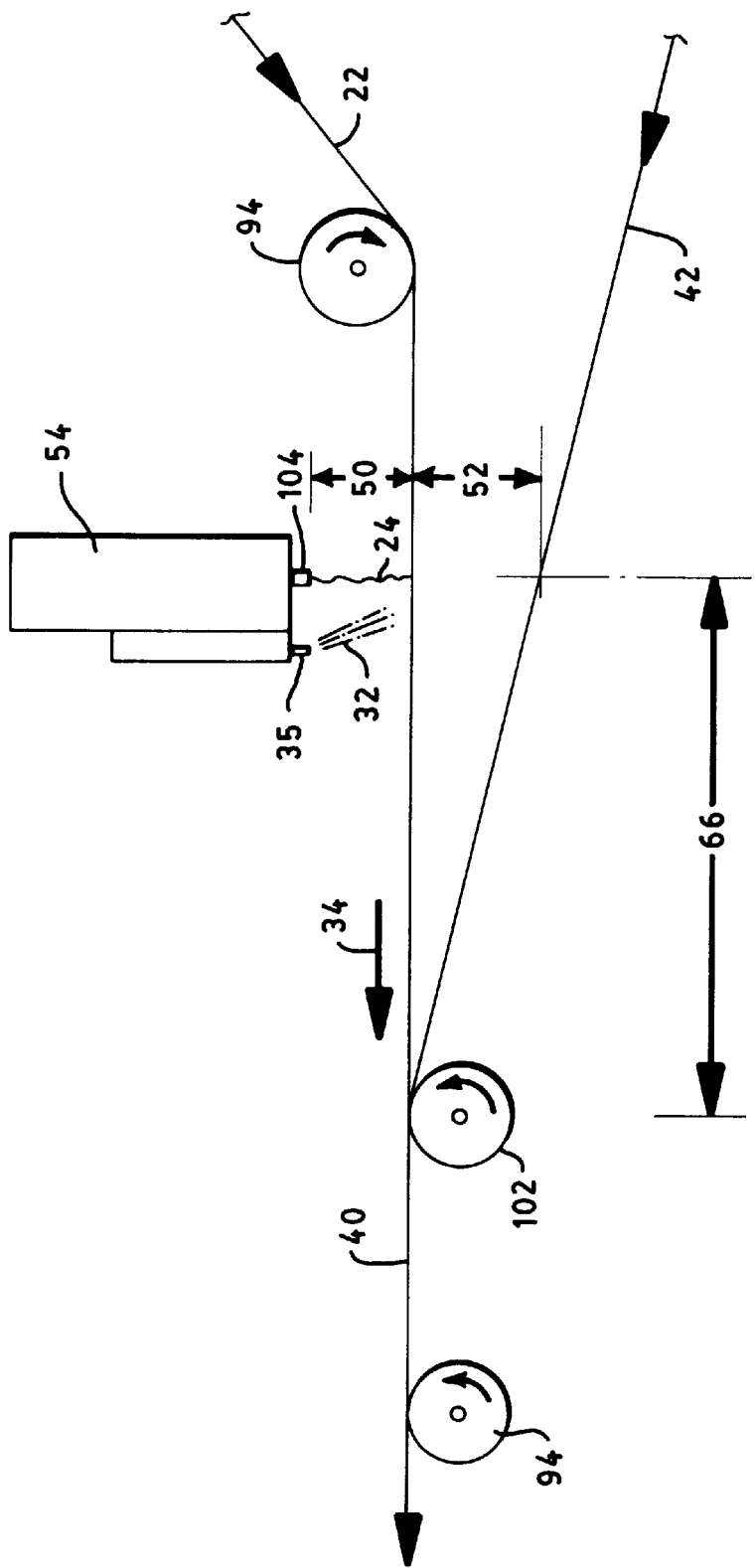
FIG. 10 representatively shows a schematic, side view of an adhesive applicator system of the invention.

With reference to FIGS. 10, 12 and 12A, a further aspect of the invention can include a moving of a strand of material, such as the shown material strand 22, at a selected speed along its appointed machine-direction 34. A substantially continuous filament 24, such as a filament of adhesive, can be directed onto the strand of material along an oscillating filament path 26, and the filament 24 can be arranged to provide a plurality of filament threads extending, or otherwise disposed, from opposed lateral side regions 30 of the strand of material 22. An air stream 32 can also be directed to operatively rope or otherwise wrap the filament threads around the strand of material 22. Desirably, a majority of the filament threads are wrapped around their corresponding strand of material. More desirably, substantially all of the filament threads are wrapped around their corresponding strand 22.

In particular aspects of the invention, the filament can be arranged to provide a plurality of overlaps between the filament 24 and its corresponding strand 22. The overlaps can, for example, extend generally cross-wise of the strand, and can be arranged in a selected series or other pattern along the longitudinal, machine-direction length of their corresponding strand. In other aspects of the invention, the air stream 32 can be directed to break or otherwise separate the filament 24 into thread segments that are attached in the cross-wise alignment onto their corresponding strand of material.

In still other aspects, the directing of the substantially continuous filament of adhesive 24 onto the strand of material 22 can provide the filament threads in the form of a plurality of filament arches 28 which extend from or are otherwise disposed at the lateral side regions 30 of the strand of material 22. Desired arrangements of the adhesive filament can provide a plurality of substantially continuous filament arches, and the arches may be arranged in an alternating, staggered pattern with respect to their corresponding, individual strand of material. In further aspects, the technique of the invention can further include a contacting of the strand of material and wrapped adhesive onto a selected substrate, such as the base layer 42, to form a substrate composite 40.

A suitable supply source, such as the representatively shown applicator 54, can direct an individual, substantially continuous filament 24 of the desired material onto each individual strand of material 22 along an individual oscillating filament path 26. In the representatively shown arrangement, the selected filament is composed of adhesive. The position of the adhesive filament 24 is reciprocated in a substantially continuous, backand-forth motion to provide the desired oscillating filament path 26 which crosses over the material strand 24 and extends past the cross-directionally opposed, lateral side regions 30 of the strand. The combination of the oscillating filament path and the machine-directional movement of the strand of material can cooperate to form a plurality of filament threads, such as the representatively shown filament arches 28, which are serially disposed at and extend from the laterally opposed side regions 30 of each individual strand of material. With respect to each individual strand of material, the positioning of the resulting series or sequence of filament arches alternates from one side of the material strand to the other side of the strand. Along the longitudinal machine-direction of the strand, the immediately adjacent arches are offset and staggered from each other by approximately one-half cycle of their corresponding, oscillating filament path 26.

The desired air stream 32 can be provided by any conventional air directing mechanism, such as a nozzle, tube, orifice, annulus, deflector, vane or the like, as well as combinations thereof. With reference to FIG. 10, the mechanism for delivering the air stream 32 may include a system of air jetting nozzles 35 which are separately constructed from the first applicator 54. Alternatively, the air jetting nozzles 35 may be configured as integrated portions or components of the first applicator 54 (e.g. FIGS. 11 through 11B).

The applicator 54 may, for example, include a system of air jets which extrude or otherwise help to draw the desired adhesive filament 24 from the applicator. The system of air jets may also be employed to substantially simultaneously provide the desired air streams 32 for wrapping the desired portions of the adhesive filaments 24 about their corresponding material strands 22. Accordingly, the directing of the air stream can be conducted in cooperation with the directing of the filament of adhesive. In the various configurations of the invention, each air jet 35 and its corresponding air stream 32 can be oriented generally perpendicular to the local machine-direction 34. In particular arrangements of the invention, the air jet 35 and associated air stream 32 may be selectively tilted or otherwise angled along the machine-direction, and the amount of angle can be within the range of about ±45° relative to a line that is perpendicular to the local machine-direction, as representatively shown in FIG. 10.

Figure 11:
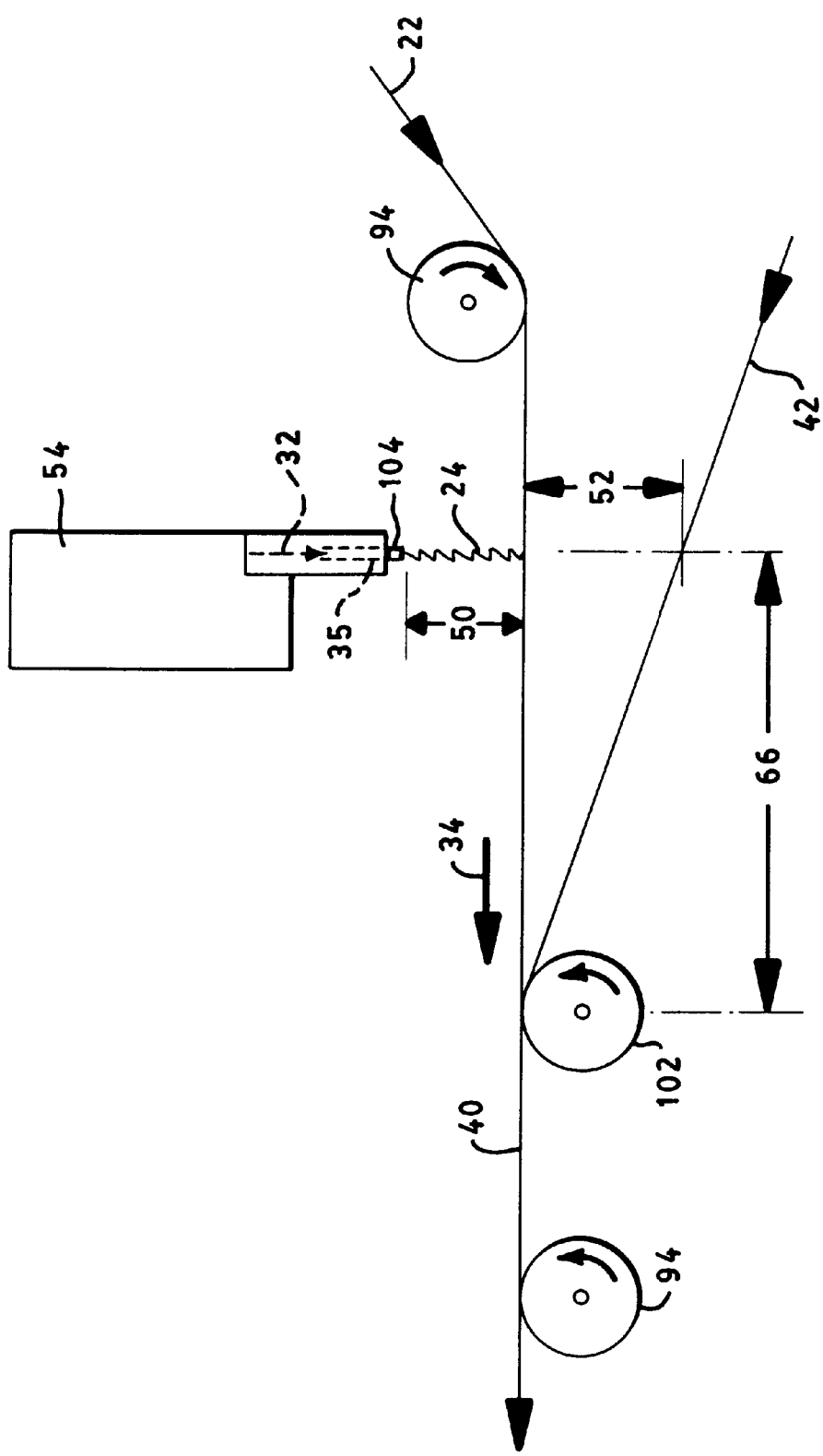
FIG. 11 representatively shows a schematic, side view of another adhesive applicator system of the invention having an array of applicator nozzles which are integrally constructed and configured with a cooperating array of air jet nozzles.
Figure 11A:
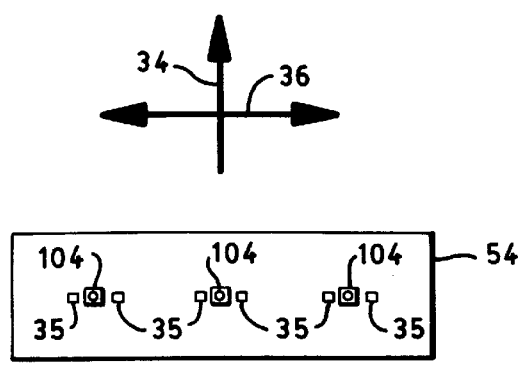
FIG. 11A representatively shows a schematic, bottom view of the adhesive applicator system illustrated in FIG. 11.

With reference to FIGS. 10 and 11, particular aspects of the invention can provide a selected gap distance 50 between the applicator nozzles 104 and their corresponding material strands 22 (also strands 56, and/or 62). In particular aspects, the nozzle-strand gap distance 50 can be at least a minimum of about 4 mm. The nozzle-strand gap distance can alternatively be at least about 8 mm, and optionally, can be at least about 12 mm to provided improved performance. In other aspects, the nozzle-strand gap distance 50 can be not more than a maximum of about 28 mm. The nozzle-strand gap distance can alternatively be not more than about 24 mm, and optionally, can be not more than about 20 mm to provide improved effectiveness. For example, the nozzle-strand distance 50 can be important for regulating the size and distribution of the filament threads or arches 28 along the lateral side regions of each material strand.

In another aspect of the invention, the technique can provide a gap distance 52 between the material strands and their associated substrate layer, such as the base layer 42 and/or the laminate composite 48. In desired configurations, the gap distance 52 can be at least a minimum of about 3 mm. The gap distance can alternatively be at least about 4 mm, and optionally, can be at least about 5 mm to provided improved performance. In other aspects, the gap distance 52 can be not more than a maximum of about 12 mm. The gap distance can alternatively be not more than about 9 mm, and optionally, can be not more than about 7 mm to provide improved effectiveness. For example, the strandsubstrate gap distance 52 should be large enough to obtain the desired wrapping of each individual adhesive filament 24 around its corresponding material strand.

Still other aspects of invention can provide a selected machine-direction, separation distance 66 between the location of the applicator nozzles 104 and the location of their associated assembly mechanism (e.g. assembly roller). In particular aspects, the separation distance 66 can be at least a minimum of about 15 cm. The separation distance 66 can alternatively be at least about 20 cm, and optionally, can be at least about 25 cm to provided improved performance. In other aspects, the separation distance 66 can be not more than a maximum of about 200 cm. The separation distance 66 can alternatively be not more than about 125 cm , and optionally, can be not more than about 25 cm to provide improved effectiveness.

The nozzle-assembly, separation distance 66 is desirably selected to allow the desired wrapping of adhesive about the material strands while also minimizing the time between the adhesive application and the contacting of the material strand and wrapped adhesive onto its corresponding, selected substrate. In particular aspects, the time between the application of the adhesive filament and the assembly of the material strand can provide a applicator-assembly time which is at least a minimum of about 0.003 sec. The applicator assembly time can alternatively be at least about 0.004 sec, and optionally, can be at least about 0.005 sec to provided improved performance. In other aspects, the applicator-assembly time can be not more than a maximum of about 0.060 sec. The applicator-assembly time can alternatively be not more than about 0.025 sec, and optionally, can be not more than about 0.015 sec to provide improved effectiveness.

In further aspects, the contacting of the adhesive wrapped material strands onto their corresponding substrate can be arranged to provide a relatively small contacting force between the material strands and substrate. In particular arrangements, the technique of the invention is configured to gently provide a substantially zero gap between the material strands and its associated substrate at the location of the corresponding assembly mechanism. For example, the gap between the material strand and its associated substrate can be arranged to lightly "kiss" the material strands onto their corresponding substrate.

Figure 11B:
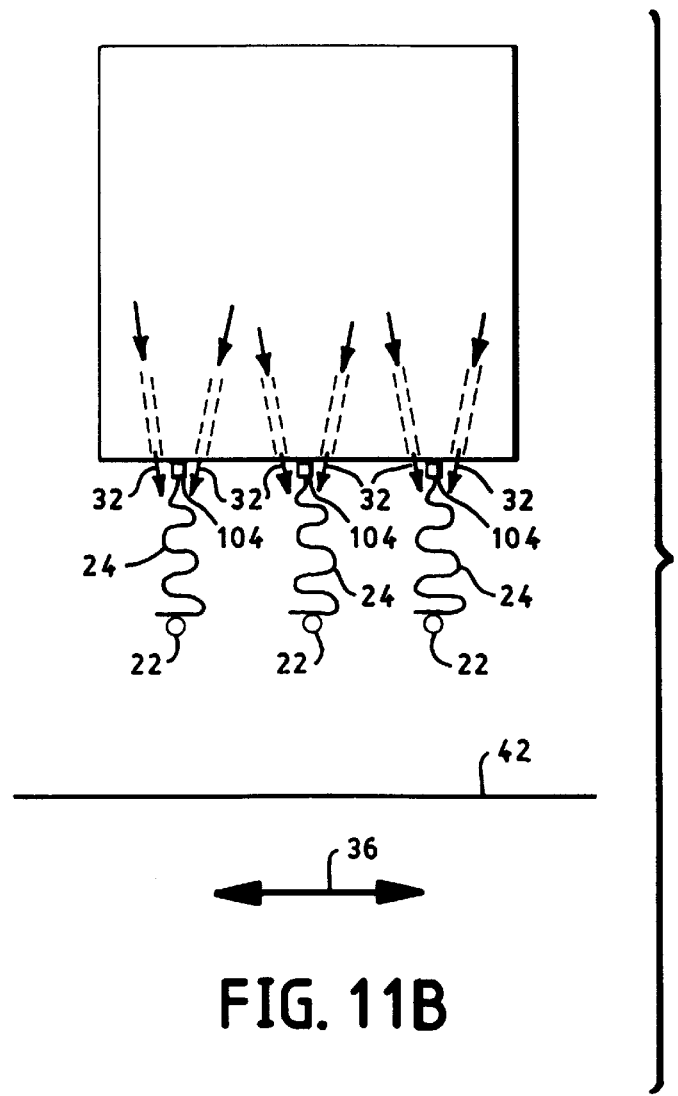
FIG. 11B representatively shows a schematic, front view of an aspect of the adhesive applicator system illustrated in FIG. 11, wherein an array of applicator nozzles are aligned along a cross-direction of the system, and an associated array of cooperating air jet nozzles are aligned and angled along the cross-direction.
Figure 13:
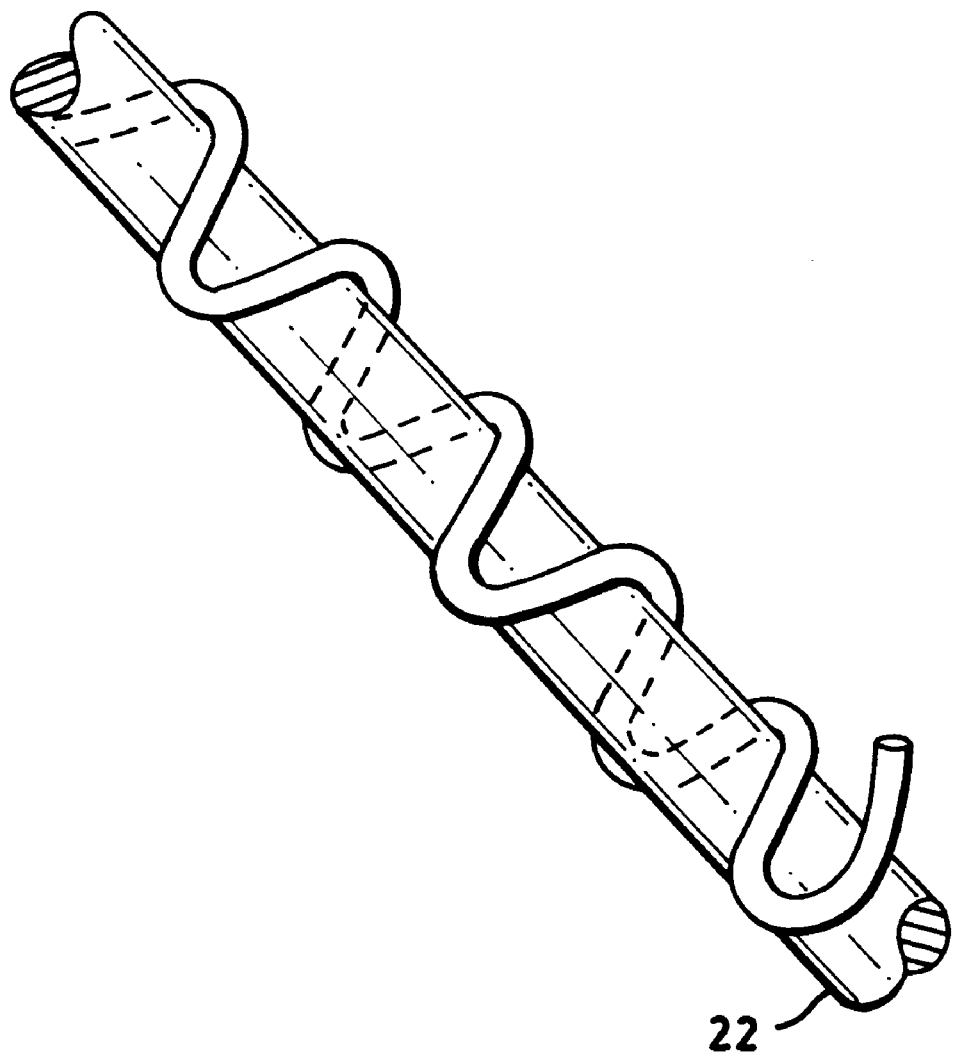
FIG. 13 representatively shows a schematic, perspective view of a strand of material wrapped with an adhesive filament.

With reference to FIGS. 11 through 11B the applicator 54 may include a plurality of applicator nozzles 104, and each applicator nozzle can have an associated system of immediately adjacent air jets 35. The applicator nozzles 104 and the air jets 35 are aligned generally along the local cross-direction 36, and each applicator nozzle 104 has a cooperating pair of air jets 35. An air jet is located at each cross-directional, lateral side of its corresponding applicator nozzle, and each air jet is oriented generally perpendicular to the local machine-direction 34. In particular arrangements of the invention, the air jets 35 and their associated air streams 32 may be selectively tilted or otherwise angled along the cross-direction, and the amount of angle can be within the range of about ±15° relative to a line that is perpendicular to the local machine-direction (e.g. FIG. 11B). In desired arrangements, each air jet can be tilted by the selected angle to direct its air stream in a direction that is slanted toward its corresponding applicator nozzle.

In the various configurations of the invention, the desired temperature of the employed adhesive can depend on the particular composition of the adhesive material. It has been found that a warmer temperature provides a relatively better distribution pattern of the adhesive filaments 24. If the adhesive temperature, however, is too high, the adhesive can excessively degrade and the adhesive filament 24 may exhibit excessive breakage.

In particular aspects, the material of the filament 24 can be provided at a viscosity which is at least a minimum of about 6,000 centipoise (cP). The viscosity can alternatively be at least about 12,000 cP, and optionally, can be at least about 16,000 cP to provided improved performance. In other aspects, the viscosity can be not more than a maximum of about 50,000 cP. The viscosity can alternatively be not more than about 22,000 cP, and optionally, can be not more than about 19,000 cP to provide improved effectiveness.

In additional aspects, the filament 24 can be provided at a filaments speed which is at least a minimum of about 0.04 m/sec. The filaments speed can alternatively be at least about 0.06 m/sec, and optionally, can be at least about 0.3 m/sec to provided improved performance. In other aspects, the filaments speed can be not more than a maximum of about 5 m/sec. The filaments speed can alternatively be not more than about 3 m/sec, and optionally, can be not more than about 1.4 m/sec to provide improved effectiveness.

The air pressure delivered to the various adhesive applicators can be provided at a selected pressure. In particular aspects, the directing of the air stream 32 can include an expelling of the air stream under an air pressure which can be at least a minimum of about 7 KPa (gauge). The air pressure can alternatively be at least about 20 KPa, and optionally, can be at least about 27 KPa to provided improved performance. In other aspects, the air pressure can be not more than a maximum of about 140 KPa. The air pressure can alternatively be not more than about 103 KPa, and optionally, can be not more than about 55 KPa to provide improved effectiveness.

If the pressure is too low, the adhesive filaments 24 may not be distributed in the desired oscillating pattern, and there may be insufficient wrapping of the adhesive filaments about their corresponding material strands. A relatively higher pressure can provide a larger distribution pattern over a greater cross-directional distance. The greater air pressure, however, can produce a finer, relatively smaller diameter adhesive filament 24, but the higher air pressure may generate excessive "blow-by" of the adhesive in a separation away from the corresponding material strands.

In particular aspects, the directing of the air stream 32 can provide an air stream speed which is at least a minimum of about 38 m/sec. The air stream speed can alternatively be at least about 190 m/sec, and optionally, can be at least about 380 m/sec to provided improved performance. In other aspects, the air stream speed can be not more than a maximum of about 3800 m/sec. The air stream speed can alternatively be not more than about 1900 m/sec, and optionally, can be not more than about 800 m/sec to provide improved benefits.

The directing of the filament of adhesive 24 along the oscillating filament path 26 can extend over an overall, cross-directional traversing distance 38 (e.g. FIG. 12) which can be at least a minimum of about 0.01 cm. The traversing distance can alternatively be at least about 0.1 cm, and optionally, can be at least about 0.2 cm to provided improved performance. In other aspects, the traversing distance can be not more than a maximum of about 0.6 cm. The traversing distance can alternatively be not more than about 0.5 cm, and optionally, can be not more than about 0.4 cm to provide improved effectiveness. In desired configurations, the oscillating filament path 26 can operatively traverse the filament 24 past both laterally opposed side regions 30 of the selected material strand by substantially equal distances.

In still other aspects, the filament path 26 can be configured to reciprocate back-and-forth at a traversing frequency which can be at least a minimum of about 100 Hz (Hertz). The frequency can alternatively be at least about 500 Hz, and optionally, can be at least about 1,000 Hz to provided improved performance. In other aspects, the frequency can be not more than a maximum of about 10,000 Hz. The frequency can alternatively be not more than about 6,000 Hz, and optionally, can be not more than about 4,500 Hz to provide improved effectiveness. In a desired configuration, the frequency can be about 1200 Hz.

The directing and depositing of the filament of adhesive 24 onto the selected strand of material can provide an adhesive add-on which can be at least a minimum of about 0.004 grams of adhesive per meter of length of the corresponding strand material (g/m). The adhesive add-on can alternatively be at least about 0.008 g/m, and optionally, can be at least about 0.012 g/m to provided improved performance. In other aspects, the adhesive add-on can be not more than a maximum of about 0.24 g/m. The adhesive add-on can alternatively be not more than about 0.07 g/m, and optionally, can be not more than about 0.04 g/m to provide improved effectiveness.

The air stream 32 can be directed to operatively wrap a substantial majority of the filament arches 28 around their corresponding strand of material 22. In particular aspects, the directing of the air stream 32 can operatively deposit and maintain at least about 60% of the filament threads or arches 28 onto their corresponding material strands (e.g. strands 22, 56 and/or 62). Alternatively, the directing of the air stream 32 can operatively deposit at least about 75% of the filament threads onto their selected strands of material, and optionally can operatively deposit at least about 90% of the filament threads onto their selected strands of material. In desired configurations, the directing of the air stream can operatively deposit substantially 100% of the filament threads onto their selected material strands.

In other aspects, the directing of the air stream 32 can be configured to detach not more than about 40 wt % of the directed adhesive away from the corresponding strands of material. The directing of the air stream can alternatively detach not more than about 25 wt % of the directed adhesive away from the strand of material, and optionally, can detach not more than about 10 wt % of the directed adhesive away from the corresponding strands of material.

In further aspects, the moving of the selected strand of material can provide a strand speed which is at least a minimum of about 0.05 m/sec. The strand speed can alternatively be at least about 0.25 m/sec, and optionally, can be at least about 3 m/sec to provided improved performance. In other aspects, the strand speed can be not more than a maximum of about 10 m/sec. The strand speed can alternatively be not more than about 6 m/sec, and optionally, can be not more than about 5 m/sec to provide improved effectiveness.

While various aspects or features of the invention have been described with respect to the particular applicator 54, it should be readily apparent that such features may be incorporated at various other locations within the technique of the invention. For example, the features may be additionally or alternatively incorporated at the locations of applicators 58 and/or 64. Suitable applicator devices can include an ITW Model, OMEGA UFD device, as previously described in detail.

It should be readily appreciated that the specific variations arrangements, locations, alignments and other operating conditions of the mechanical components on any production line can affect the operation of the overall applicating system. Accordingly, adjustments are ordinarily needed to "tune" the operation to the specific conditions. When employing an ITW Model, OMEGA UFD adhesive applicator, it has been found that the system can be tuned by adjusting the air pressure delivered to the devices and observing the amount of adhesive that is blown past the moving strands of material and collected on an underlying observation plate. The air pressure is typically adjusted under substantially all of the adhesive delivered from the applicator nozzles remains on the moving strands and approximately zero adhesive is blown past and away from the strands, and onto the observation plate.

Having described the invention in rather full detail, it will be readily apparent that various changes and modifications can be made without departing from the spirit of the invention. All of such changes and modifications are contemplated as being within the scope of the invention as defined by the subjoined claims.

We claim:

1. A method for forming an article, said method comprising:
    a moving of at least one first strand of material at a selected speed along its appointed machine-direction;
    a directing of an individual, substantially continuous filament of adhesive onto each said first strand of material along an oscillating filament path, each said filament of adhesive forming a plurality of adhesive filament threads extending from each lateral side of their corresponding strand of material;
    a directing of at least one, first air stream to operatively wrap said filament threads around their corresponding strand of material;
    a providing of a base layer of material;
    an attaching of said at least one first strand of material and its wrapped filament threads onto said base layer; and
    a dividing of said at least one first strand of material into a plurality of first strand segments to provide a substantially nongathering section of the at least one first strand of material, wherein said dividing is provided after the attaching of said at least one first strand of material onto said base layer.

2. A method as recited in claim 1, further including
    a placing of a laminate layer adjacent said at least one first strand of material;
    a moving of at least one second strand of material along its appointed machine-direction;
    an attaching of said at least one second strand of material to said base layer; and
    a folding of a portion of said base layer to substantially enclose said at least one first strand, its wrapped adhesive filament threads and said laminate layer with said base layer.

3. A method as recited in claim 1, wherein said dividing of the at least one first strand to provide its substantially nongathering section includes an ultrasonic dividing operation.

4. A method as recited in claim 1, wherein said dividing of said at least one first strand of material in said substrate composite into a plurality of strand segments includes a dividing of said at least one first strand of material with an ultrasonic component;
    said ultrasonic component having a plurality of raised portions and a plurality of relatively lowered portions;
    said raised portions configured to contact said substrate composite to provide said dividing of said at least one first strand of material; and said lowered portions including low-adhesion material disposed therein.

5. A method as recited in claim 4, wherein said low-adhesion material is a silicone rubber material.

6. A method as recited in claim 4, wherein said ultrasonic component is a rotary component having an array of raised portions distributed along an outer, circumferential periphery of said component.

7. A method as recited in claim 1, further comprising an additional bonding of said at least one first strand to said base layer adjacent a longitudinal end of its substantially nongathering section.

8. A method as recited in claim 7, wherein said additional bonding of the at least one first strand adjacent said longitudinal end of its substantially nongathering section includes an ultrasonic bonding operation.

9. A method as recited in claim 1, wherein said directing of said substantially continuous filament of adhesive onto each said first strand of material provides a plurality of substantially continuous first filament arches extending from said lateral side regions of each said first strand of material.

10. A method as recited in claim 9, wherein said directing of said at least one, first air stream operatively wraps a majority of said first filament arches around their corresponding strand of material.

11. A method as recited in claim 1, wherein said directing of said individual, substantially continuous filament of adhesive onto each said first strand of material along said oscillating filament path traverses said filament of adhesive over a traversing distance of at least about 0.2 cm.

12. A method as recited in claim 1, wherein said directing of said individual, substantially continuous filament of adhesive onto each said first strand of material along said oscillating filament path traverses said filament of adhesive with a traversing frequency of at least about 100 Hz.

13. A method as recited in claim 2, further comprising:
a directing of an individual, substantially continuous second filament of adhesive onto each said second strand of material along an individual oscillating filament path, each said second filament arranged to form a second plurality of filament arches extending from each lateral side of their corresponding strand of material;
a directing of at least ones second air stream to operatively wrap a majority of said second filament arches around their corresponding strand of material; and
a placing of said at least one second strand of material and its wrapped filament arches onto said base layer.

14. A method as recited in claim 13, further comprising a dividing of said at least form a plurality of second strand segments to provide a substantially nongathering section of said at least one second strand of material, wherein said dividing of said at least one second strand is provided after the attaching of said at least one second strand to said base layer.

15. A method as recited in claim 14, further comprising an additional bonding of said at least one second strand to said base layer adjacent a longitudinal end of its corresponding substantially nongathering section.

16. A method as recited in claim 15, wherein said additional bonding of the at least one second strand adjacent the longitudinal end of its corresponding substantially nongathering section includes an ultrasonic bonding operation.

17. A method as recited in claim 2, further comprising:
a moving of at least one, third strand of material along its appointed machine-direction; and
an attaching of said at least one third strand of material to said laminate layer; and wherein
said folding of said portion of said base layer substantially encloses said at least one third strand with said base layer.

18. A method as recited in claim 17, further comprising:
a moving of a plurality of third strands of material along their appointed machine-direction;
a directing of an individual, substantially continuous filament of adhesive onto each said third strand of material along an oscillating filament path, each said filament arranged to form a plurality of filament arches extending from each lateral side of their corresponding third strand of material;
a directing of at least one air stream to operatively wrap a majority of said filament arches around their corresponding third strand of material; and
a placing of said plurality of said third strands of material and their wrapped adhesive filament arches onto said base layer; and wherein
said folding of said portion of said base layer substantially encloses said plurality of said third strands and their wrapped adhesive filament arches with said base layer.

19. A method as recited in claim 18, further comprising a dividing of said third strands of material to form a plurality of third strand segments, to provide a substantially nongathering section of said plurality of third strands of material, wherein said dividing of said plurality of third strands of material is provided after the attaching of said plurality of third strands to said base layer.

20. A method as recited in claim 2, further including a folding of another portion of said base layer to substantially enclose said at least one second strand.

* * * * *

UNITED STATES PATENT AND TRADEMARK OFFICE
CERTIFICATE OF CORRECTION

PATENT NO. : 6,235,137 B1
DATED : May 22, 2001
INVENTOR(S) : David James Van Eperen et al.

It is certified that error appears in the above-identified patent and that said Letters Patent is hereby corrected as shown below:

<u>Title page,</u>
Item [56],
Line 9, before the word "Werenicz", delete "6/1989", and substitute -- 10/1992 --.
Line 11, before the word "Kellenberger", delete "9/1992" and substitute -- 3/1998 --.

<u>Column 14,</u>
Line 52, delete "20".

<u>Column 15,</u>
Line 10, after the word "direction", insert -- 34 --.
Line 60, between the words "that" and "generally", insert -- are --.

<u>Column 16,</u>
Line 5, delete "15".

<u>Column 23,</u>
Line 26, delete "ones", and substitute -- one --.
Line 32, after the phrase "at least", insert -- one second strand of material to --.

Signed and Sealed this

Eighth Day of January, 2002

*Attest:*

JAMES E. ROGAN
*Attesting Officer*  *Director of the United States Patent and Trademark Office*